US011976122B2

(12) United States Patent
Van Berkel et al.

(10) Patent No.: US 11,976,122 B2
(45) Date of Patent: *May 7, 2024

(54) ANTI-IL13Rα2 ANTIBODIES

(71) Applicant: ADC THERAPEUTICS SA, Epalinges (CH)

(72) Inventors: Patricius Hendrikus Cornelis Van Berkel, Epalinges (CH); Francois Bertelli, Epalinges (CH)

(73) Assignee: ADC THERAPEUTICS SA, Epalinges (CH)

( * ) Notice: Subject to any disclaimer, the term of this patent is extended or adjusted under 35 U.S.C. 154(b) by 46 days.

This patent is subject to a terminal disclaimer.

(21) Appl. No.: 17/389,582

(22) Filed: Jul. 30, 2021

(65) Prior Publication Data

US 2022/0033508 A1 Feb. 3, 2022

(30) Foreign Application Priority Data

Jul. 31, 2020 (GB) ..................... 2011993

(51) Int. Cl.
*C07K 16/28* (2006.01)
*A61K 47/68* (2017.01)

(52) U.S. Cl.
CPC ...... *C07K 16/2866* (2013.01); *A61K 47/6801* (2017.08); *C07K 2317/55* (2013.01)

(58) Field of Classification Search
CPC ............ C07K 16/2866; C07K 2317/55; C07K 2317/92; C07K 14/7155; A61K 47/6801
See application file for complete search history.

(56) References Cited

U.S. PATENT DOCUMENTS

| | | | |
|---|---|---|---|
| 4,816,567 A | 3/1989 | Cabilly et al. | |
| 5,595,756 A * | 1/1997 | Bally ................. | A61K 9/1272 264/4.1 |
| 6,428,788 B1 | 8/2002 | Debinski et al. | |
| 7,338,929 B2 | 3/2008 | Debinski et al. | |
| 7,521,541 B2 | 4/2009 | Eigenbrot et al. | |
| 7,541,040 B2 | 6/2009 | Puri et al. | |
| 7,612,181 B2 | 11/2009 | Wu et al. | |
| 7,666,411 B2 | 2/2010 | Strober et al. | |
| 7,723,485 B2 | 5/2010 | Junutula et al. | |
| 7,960,361 B2 | 6/2011 | Debinski et al. | |
| 7,999,083 B2 | 8/2011 | Govindan et al. | |
| 8,080,250 B1 | 12/2011 | Govindan et al. | |
| 8,173,123 B2 | 5/2012 | Strober et al. | |
| 8,258,268 B2 | 9/2012 | Wu et al. | |
| 8,435,534 B2 | 5/2013 | Debinski et al. | |
| 8,771,988 B2 | 7/2014 | Goepfert et al. | |
| 8,821,866 B2 | 9/2014 | Strober et al. | |
| 8,877,202 B2 | 11/2014 | Govindan et al. | |
| 8,937,161 B2 | 1/2015 | Mao et al. | |
| 8,999,344 B2 | 4/2015 | Govindan et al. | |
| 9,095,628 B2 | 8/2015 | Govindan et al. | |
| 9,198,978 B2 | 12/2015 | Govindan et al. | |
| 9,302,015 B2 | 4/2016 | Papadopoulos et al. | |
| 9,629,926 B2 | 4/2017 | Govindan et al. | |
| 9,770,517 B2 | 9/2017 | Govindan et al. | |
| 9,828,428 B2 | 11/2017 | Ma et al. | |
| 9,914,909 B2 | 3/2018 | Brown et al. | |
| 9,919,056 B2 | 3/2018 | Van Berkel et al. | |
| 9,931,414 B2 | 4/2018 | Van Berkel et al. | |
| 9,931,415 B2 | 4/2018 | Van Berkel et al. | |
| 9,950,078 B2 | 4/2018 | Howard et al. | |
| 9,956,299 B2 | 5/2018 | Howard et al. | |
| 10,010,624 B2 | 7/2018 | Howard et al. | |
| 10,017,580 B2 | 7/2018 | Van Berkel et al. | |
| 10,066,023 B2 | 9/2018 | Lobb et al. | |
| 10,072,075 B2 | 9/2018 | Koenig et al. | |
| 10,137,196 B2 | 11/2018 | Govindan et al. | |
| 10,508,143 B1 | 12/2019 | Lobb et al. | |
| 10,544,223 B2 | 1/2020 | Van Berkel et al. | |
| 10,695,433 B2 | 6/2020 | Van Berkel et al. | |
| 10,736,903 B2 | 8/2020 | Van Berkel et al. | |
| 10,751,346 B2 | 8/2020 | Van Berkel et al. | |
| 10,752,667 B2 | 8/2020 | Debinski et al. | |
| 10,780,096 B2 | 9/2020 | Van Berkel et al. | |
| 10,799,597 B2 | 10/2020 | Goldenberg | |
| 10,851,169 B2 | 12/2020 | Balyasnikova et al. | |
| 10,954,305 B2 | 3/2021 | Chang et al. | |
| 11,111,291 B2 | 9/2021 | Famili et al. | |
| 11,160,872 B2 | 11/2021 | Van Berkel | |
| 2005/0112130 A1 | 5/2005 | Bhat et al. | |
| 2005/0288491 A1 | 12/2005 | Wilson et al. | |

(Continued)

FOREIGN PATENT DOCUMENTS

| | | |
|---|---|---|
| CN | 101585880 A | 11/2009 |
| EP | 2500352 A1 | 9/2012 |

(Continued)

OTHER PUBLICATIONS

Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Greenspan et al., 1999, Defining epitopes: It's not as easy as it seems; Nature Biotechnology, 17:936-937 (Year: 1999).*
Bork. Powers and Pitfalls in Sequence Analysis: The 70% Hurdle. Genome Research, 2000, 10:398-400 (Year: 2000).*
Janeway et al., Immunobiology: The Immune System in Health and Disease, 5th edition New York: Garland Science; 2001 (Year: 2001).*

(Continued)

*Primary Examiner* — Vanessa L. Ford
*Assistant Examiner* — Danaya L Middleton
(74) *Attorney, Agent, or Firm* — MEDLER FERRO WOODHOUSE & MILLS PLLC

(57) ABSTRACT

This disclosure relates to antibodies that specifically bind to the Interleukin-13 receptor subunit alpha-2 (IL13Rα2) protein, and associated uses and methods for production.

13 Claims, 2 Drawing Sheets

Specification includes a Sequence Listing.

(56) References Cited

U.S. PATENT DOCUMENTS

| | | |
|---|---|---|
| 2007/0212337 A1 | 9/2007 | Bedi et al. |
| 2008/0206239 A1 | 8/2008 | Jones et al. |
| 2012/0195900 A1 | 8/2012 | Ghayur et al. |
| 2012/0201746 A1 | 8/2012 | Liu et al. |
| 2015/0079135 A1 | 3/2015 | Cirrito et al. |
| 2015/0266962 A1 | 9/2015 | Ma et al. |
| 2015/0273077 A1 | 10/2015 | Van Berkel et al. |
| 2016/0095939 A1 | 4/2016 | Goldenberg |
| 2016/0256561 A1 | 9/2016 | Howard et al. |
| 2016/0361360 A1 | 12/2016 | Chang et al. |
| 2018/0086828 A1 | 3/2018 | Van Berkel et al. |
| 2018/0092985 A1 | 4/2018 | Van Berkel et al. |
| 2018/0092986 A1 | 4/2018 | Van Berkel et al. |
| 2018/0099055 A1 | 4/2018 | Van Berkel et al. |
| 2018/0117172 A1 | 5/2018 | Van Berkel et al. |
| 2018/0125994 A1 | 5/2018 | Van Berkel et al. |
| 2018/0127505 A1 | 5/2018 | Van Berkel et al. |
| 2018/0142025 A1 | 5/2018 | Van Berkel |
| 2018/0170992 A1 | 6/2018 | Balyasnikova et al. |
| 2018/0194861 A1 | 7/2018 | Dong et al. |
| 2018/0303953 A1 | 10/2018 | Van Berkel et al. |
| 2018/0333504 A1 | 11/2018 | Han et al. |
| 2019/0010242 A1 | 1/2019 | Eckelman et al. |
| 2019/0031772 A1 | 1/2019 | Cirrito et al. |
| 2019/0330366 A1 | 10/2019 | Eckelman et al. |
| 2020/0031947 A1* | 1/2020 | Bucktrout .......... C07K 16/2878 |
| 2020/0048350 A1 | 2/2020 | Eckelman et al. |
| 2020/0069814 A1 | 3/2020 | Zhao et al. |
| 2020/0079867 A1 | 3/2020 | Watkins et al. |
| 2020/0129638 A1 | 4/2020 | Van Berkel et al. |
| 2020/0171164 A1 | 6/2020 | Feingold et al. |
| 2020/0222547 A1 | 7/2020 | Stark et al. |
| 2020/0276261 A1 | 9/2020 | Zhao et al. |
| 2020/0306375 A1 | 10/2020 | Lobb et al. |
| 2020/0316218 A1 | 10/2020 | Germeroth et al. |
| 2020/0362054 A1 | 11/2020 | Granda et al. |
| 2020/0390889 A1 | 12/2020 | Horner et al. |
| 2020/0405872 A1 | 12/2020 | Feingold et al. |
| 2020/0405873 A1 | 12/2020 | Feingold et al. |
| 2020/0405879 A1 | 12/2020 | Feingold et al. |
| 2021/0010089 A1 | 1/2021 | Marine et al. |
| 2021/0032661 A1 | 2/2021 | Powell et al. |
| 2021/0079020 A1 | 3/2021 | Van Berkel |
| 2021/0169896 A1 | 6/2021 | Zhao et al. |
| 2021/0221895 A1 | 7/2021 | Balyasnikova et al. |
| 2021/0322564 A1 | 10/2021 | Zammarchi et al. |
| 2021/0363224 A1 | 11/2021 | Casal Alvarez et al. |
| 2022/0016259 A1 | 1/2022 | Van Berkel et al. |
| 2022/0062352 A1 | 3/2022 | Proehl et al. |
| 2022/0105190 A1 | 4/2022 | Lockshin |

FOREIGN PATENT DOCUMENTS

| | | |
|---|---|---|
| EP | 2500353 A2 | 9/2012 |
| EP | 3450460 A1 | 3/2019 |
| EP | 3480212 A1 | 5/2019 |
| WO | 1999036437 A1 | 7/1999 |
| WO | 2003092717 A1 | 11/2003 |
| WO | 2007024715 A2 | 3/2007 |
| WO | 2014057118 A1 | 4/2014 |
| WO | 2014152361 A1 | 9/2014 |
| WO | 2014163684 A1 | 10/2014 |
| WO | 2015126548 A1 | 8/2015 |
| WO | 2016123142 A1 | 8/2016 |
| WO | 2016166305 A1 | 10/2016 |
| WO | 2016210108 A1 | 12/2016 |
| WO | 2017137556 A1 | 8/2017 |
| WO | 2017185662 A1 | 11/2017 |
| WO | 2017210058 A1 | 12/2017 |
| WO | 2018102795 A2 | 6/2018 |
| WO | 2018187791 A1 | 10/2018 |
| WO | 2018217227 A1 | 11/2018 |
| WO | 2019091384 A1 | 5/2019 |
| WO | 2019094395 A2 | 5/2019 |
| WO | 2019155000 A1 | 8/2019 |
| WO | 2019224275 A1 | 11/2019 |
| WO | 2020011724 A1 | 1/2020 |
| WO | 2020052692 A2 | 3/2020 |
| WO | 2020073345 A1 | 4/2020 |
| WO | 2020109251 A1 | 6/2020 |
| WO | 2020127573 A1 | 6/2020 |
| WO | 2020155017 A1 | 8/2020 |
| WO | 2020168106 A1 | 8/2020 |
| WO | 2020219563 A1 | 10/2020 |
| WO | 2020223108 A1 | 11/2020 |
| WO | 2020236797 A1 | 11/2020 |

OTHER PUBLICATIONS

ADC Review, What is Pyrrolobenzodiazepine (PBD)?, Mar. 23, 2019, adcreview.com/knowledge-center/what-is-pyrrolobenzodiazepine-pbd/ (Year: 2019).*

Heppner et al., Tumor heterogeneity: biological implications and therapeutic consequences, 1983, Cancer Metastasis Reviews 2: 5-23 (Year: 1983).*

Jain RK, Barriers to Drug Delivery in Solid Tumors, 1994, Scientific American, pp. 58-645 (Year: 1994).*

Gura T, Systems for Identifying New Drugs are Often Faulty, Science, 1997, 278(5340): 1041-1042 (Year: 1997).*

Sporn et al. Chemoprevention of Cancer, Carcinogenesis, vol. 21 (2000), 525-530 (Year: 2000).*

Auerbach et al., Angiogenesis assays: Problems and pitfalls, Cancer and Metastasis Reviews, 2000, 19: 167-172 (Year: 2000).*

Hait., Anticancer drug development: the grand challenges, Nature Reviews/Drug Discovery, 2010, 9, pp. 253-254 (Year: 2010).*

Gravanis et al., The changing world of cancer drug development: the regulatory bodies' perspective, Chin Clin Oncol, 2014, 3, pp. 1-5 (Year: 2014).*

Beans, Targeting metastasis to halt cancer's spread, PNAS 2018; 115(50): 12539-12543 (Year: 2018).*

Altuvia et al., "Ranking potential binding peptides to MHC molecules by a computational threading approach," Journal of Molecular Biology 249(2):244-250 (1995).

Balyasnikova et al., "Characterization and immunotherapeutic implications for a novel antibody targeting interleukin (IL)-13 receptor α2," Journal of Biological Chemistry 287(36):30215-30227 (2012).

Boswell et al., "Effects of charge on antibody tissue distribution and pharmacokinetics," Bioconjugate Chemistry 21(12):2153-2163 (2010).

Carter P., "Potent antibody therapeutics by design," Nature Reviews Immunology 6(5):343-357 (2006).

Chomarat et al., "Interleukin-4 and interleukin-13: their similarities and discrepancies," International Reviews of Immunology 17(1-4):1-52 (1998).

Clackson et al., "Making antibody fragments using phage display libraries," Nature 352:624-628 (1991).

Dall'Acqua et al., "Antibody humanization by framework shuffling," Methods 36(1):43-60 (2005).

Dornan et al., "Therapeutic potential of an anti-CD79b antibody-drug conjugate, anti-CD79b-vc-MMAE, for the treatment of non-Hodgkin lymphoma," Blood 114(13):2721-2729 (2009).

Doronina et al., "Enhanced activity of monomethylauristatin F through monoclonal antibody delivery: effects of linker technology on efficacy and toxicity," Bioconjugate Chemistry 17(1):114-124 (2006).

Erickson et al., "Antibody-maytansinoid conjugates are activated in targeted cancer cells by lysosomal degradation and linker-dependent intracellular processing," Cancer Research 66(8):4426-4433 (2006).

Fujisawa et al., "A novel role of interleukin-13 receptor alpha2 in pancreatic cancer invasion and metastasis," Cancer Research 69(22):8678-8685 (2009).

Hamann P., "Monoclonal antibody-drug conjugates," Expert Opinion on Therapeutic Patents 15(9):1087-1103 (2005).

Hamblett et al., "Effects of drug loading on the antitumor activity of a monoclonal antibody drug conjugate," Clinical Cancer Research 10(20):7063-7070 (2004).

(56) References Cited

OTHER PUBLICATIONS

Jeffrey et al., "Design, synthesis, and in vitro evaluation of dipeptide-based antibody minor groove binder conjugates," Journal of Medicinal Chemistry 48(5):1344-1358 (2005).
Jespers et al., "Guiding the selection of human antibodies from phage display repertoires to a single epitope of an antigen," Bio/Technology 12(9):899-903 (1994).
Joshi et al., "Interleukin-13 receptor alpha chain: a novel tumor-associated transmembrane protein in primary explants of human malignant gliomas," Cancer Research 60(5):1168-1172 (2000).
Junutula et al., "Site-specific conjugation of a cytotoxic drug to an antibody improves the therapeutic index," Nature Biotechnology 26(8):925-932 (2008).
Kioi et al., "Interleukin-13 receptor alpha2 chain: a potential biomarker and molecular target for ovarian cancer therapy," Cancer 107(6):1407-1418 (2006).
Kohler et al., "Continuous cultures of fused cells secreting antibody of predefined specificity," Nature 256:495-497 (1975).
Kovtun et al., "Antibody-Drug Conjugates Designed to Eradicate Tumors with Homogeneous and Heterogeneous Expression of the Target Antigen," Cancer Research 66(6):3214-3221 (2006).
Lambert J., "Drug-conjugated monoclonal antibodies for the treatment of cancer," Current Opinion in Pharmacology 5(5):543-549 (2005).
Law et al., "Lymphocyte Activation Antigen CD70 Expressed by Renal Cell Carcinoma Is a Potential Therapeutic Target for Anti-CD70 Antibody-Drug Conjugates," Cancer Research 66(4):2328-2337 (2006).
Lazar et al., "A molecular immunology approach to antibody humanization and functional optimization," Molecular Immunology 44(8):1986-1998 (2007).
Lonberg N., "Fully human antibodies from transgenic mouse and phage display platforms," Current Opinion in Immunology 20(4):450-459 (2008).
Marks et al., "By-passing Immunization, Human Antibodies from V-gene Libraries Displayed on Phage," Journal of Molecular Biology 222(3):581-597 (1991).
McDonagh et al., "Engineered antibody-drug conjugates with defined sites and stoichiometries of drug attachment," Protein Engineering, Design and Selection 19(7):299-307 (2006).
Morrison et al., "Chimeric human antibody molecules: Mouse antigen-binding domains with human constant region domains," PNAS, 81(21):6851-6855 (1984).
Murata et al., "Structure of and signal transduction through interleukin-4 and interleukin-13 receptors (review)," International Journal of Molecular Medicine 1(3):551-557 (1998).
Nicolaou et al., "Calicheamicin θ 1I: A Rationally Designed Molecule with Extremely Potent and Selective DNA Cleaving Properties and Apoptosis Inducing Activity," Angewandte Chemie International Edition, 33(2):183-186 (1994).
Okamoto et al., "Interleukin-13 receptor α2 is a novel marker and potential therapeutic target for human melanoma," Scientific Reports 9(1):1281 (2019).
Payne, G., "Progress in immunoconjugate cancer therapeutics," Cancer Cell 3(3):207-212 (2003).
Sanderson et al., "In vivo drug-linker stability of an anti-CD30 dipeptide-linked auristatin immunoconjugate," Clinical Cancer Research 11(2 Pt 1):843-852 (2005).
Seyfizadeh et al., "Interleukin-13 as an important cytokine: A review on its roles in some human diseases," Acta Microbiologica et Immunologica Hungarica 62(4):341-378 (2015).
Syrigos et al., "Antibody Directed Enzyme Prodrug Therapy (ADEPT): A Review of the Experimental and Clinical Considerations," Anticancer Research 19(1A):605-613 (1999).
Trail et al., "Monoclonal antibody drug immunoconjugates for targeted treatment of cancer," Cancer Immunology, Immunotherapy 52(5):328-337 (2003).
Wu et al., "Arming antibodies: prospects and challenges for immunoconjugates," Nature Biotechnology 23(9):1137-1146 (2005).
Xie et al., "In vivo behaviour of antibody-drug conjugates for the targeted treatment of cancer," Expert Opinion on Biological Therapy 6(3):281-291 (2006).

* cited by examiner

ANTI-IL13Rα2 ANTIBODIES

EARLIER APPLICATION

This application claims priority from United Kingdom application number GB 2011993.9 filed on 31 Jul. 2020.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 16,384 bytes ASCII (Text) file named "007933831-Patent-134-WO-sequence-listing-v2-for-filing," created on Jul. 30, 2021.

FIELD

The present disclosure relates to antibodies that specifically bind to the Interleukin-13 receptor subunit alpha-2 (IL13Rα2) protein. Also disclosed are methods for the production and use of the anti-IL13Rα2 antibodies.

BACKGROUND

IL13Rα2

Interleukin-13 receptor subunit alpha-2 (IL-13Rα2; also known as cluster of differentiation 213A2, CD213A2), is a membrane bound protein that is closely related to IL-13Rα1, a subunit of the interleukin-13 type I cytokine receptor complex together with IL-4Rα.

Together, IL13Rα1 and IL-4Rα form a dimer; IL-13 binds to the IL-13Rα1 chain while IL-4Rα stabilises this interaction. This IL-13 receptor can also instigate IL-4 signalling. In both cases this occurs via activation of the Janus kinase (JAK)/Signal Transducer and Activator of Transcription (STAT) pathway, resulting in phosphorylation of STAT6. Phosphorylated STAT6 dimerises and acts as a transcription factor activating many genes, such as eotaxin. (Murata T, et al., Int J Mol Med. 1998 Mar; 1(3):551-7; Chomarat P, et al., Int Rev Immunol. 1998; 17(1-4):1-52).

IL-13Rα2 is encoded by the IL13RA2 gene. IL-13Rα2 binds IL-13 with very high affinity (and can therefore sequester it) but does not allow IL-4 binding. It acts as a negative regulator of both IL-13 and IL-4, however the mechanism of this is still undetermined (Seyfizadeh N et al, Acta Microbiol Immunol Hung. 2015 December; 62(4):341-78).

IL-13Rα2 has been found to be over-expressed in a variety of cancers, including pancreatic (Fujisawa et al, Cancer Res. 2009 Nov. 15; 69(22):8678-85), ovarian (Kioi et al, Cancer. 2006 Sep. 15; 107(6): 1407-18), melanomas (Okamoto et al, Sci Rep. 2019 Feb. 4; 9(1):1281), and malignant gliomas (Joshi et al, Cancer Res. 2000 Mar. 1; 60(5):1168-72).

Anti-IL13Rα2 antibodies

Generation of murine anti-IL13Rα2 monoclonal antibodies by immunisation of female BALB/c mice with a human recombinant IL13Rα2 fusion protein is described in Balyasnikova et al (J Biol Chem. 2012 Aug. 31; 287(36): 30215-30227). Among the murine anti-IL13Rα2 antibodies generated and characterised in this publication is the antibody designated "Clone 47".

Antibody-drug conjugates

Antibody therapy has been established for the targeted treatment of patients with cancer, immunological and angiogenic disorders (Carter, Nat Rev Immunol. 2006 May; 6(5):343-57).

Antibody-drug conjugates (ADCs), i.e. immunoconjugates, are used for local delivery of cytotoxic or cytostatic agents, i.e. drugs to kill or inhibit tumor cells, in the treatment of cancer. These provide targeted delivery of the drug moiety to tumors, and intracellular accumulation therein, whereas systemic administration of these unconjugated drug agents may result in unacceptable levels of toxicity to normal cells (Xie et al (2006) Expert. Opin. Biol. Ther. 6(3):281-291; Kovtun et al (2006) Cancer Res. 66(6): 3214-3121; Law et al (2006) Cancer Res. 66(4):2328-2337; Wu et al (2005) Nature Biotech. 23(9):1137-1145; Lambert J. (2005) Current Opin. in Pharmacol. 5:543-549; Hamann P. (2005) Expert Opin. Ther. Patents 15(9):1087-1103; Payne, G. (2003) Cancer Cell 3:207-212; Trail et al (2003) Cancer Immunol. Immunother. 52:328-337; Syrigos and Epenetos (1999) Anticancer Research 19:605-614).

Maximal efficacy with minimal toxicity is sought thereby. Efforts to design and refine ADC have focused on the selectivity of monoclonal antibodies (mAbs) as well as drug mechanism of action, drug-linking, drug/antibody ratio (loading), and drug-releasing properties (Junutula, et al., 2008b Nature Biotech., 26(8):925-932; Dornan et al (2009) Blood 114(13):2721-2729; U.S. Pat. Nos. 7,521,541; 7,723, 485; WO2009/052249; McDonagh (2006) Protein Eng. Design & Sel. 19(7): 299-307; Doronina et al (2006) Bioconj. Chem. 17:114-124; Erickson et al (2006) Cancer Res. 66(8):1-8; Sanderson et al (2005) Clin. Cancer Res. 11:843-852; Jeffrey et al (2005) J. Med. Chem. 48:1344-1358; Hamblett et al (2004) Clin. Cancer Res. 10:7063-7070). Drug moieties may impart their cytotoxic and cytostatic effects by mechanisms including tubulin binding, DNA binding, proteasome and/or topoisomerase inhibition. Some cytotoxic drugs tend to be inactive or less active when conjugated to large antibodies or protein receptor ligands.

In view of the role of IL-13Rα2 in human cancers, it is desirable to identify antibodies with advantageous properties that specifically bind IL-13Rα2. The present disclosure concerns such antibodies.

SUMMARY

The present disclosure provides humanised anti-IL13Rα2 antibodies derived from humanisation of the murine anti-IL13Rα2 antibody "Clone 47" described in Balyasnikova et al (J Biol Chem. 2012 Aug. 31; 287(36): 30215-30227).

Beginning from murine "Clone 47", the present authors have generated a number of humanised heavy and light chain sequences with a view to creating antibodies that have lower immunogenicity in a human individual than chimeric antibodies comprising the heavy and light chain sequences of the murine antibody.

Surprisingly, it was found that in addition to lower immunogenicity these humanised variants may possess other advantageous properties as compared to murine Clone 47 and/or other humanised anti-IL13Rα2 antibodies, for example improved affinity for human IL13Rα2, as outlined elsewhere herein.

Accordingly, in a first aspect, the present disclosure provides a humanised antibody that binds to Interleukin-13 receptor subunit alpha-2 (IL13Rα2), wherein the antibody comprises a heavy chain variable region comprising an amino acid sequence selected from the group consisting of: SEQ ID NO: 3; SEQ ID NO: 5; SEQ ID NO: 6; SEQ ID NO: 7; and SEQ ID NO: 8.

In some embodiments, the humanised antibody further comprises a light chain variable region comprising an amino acid sequence selected from the group consisting of: SEQ ID NO: 4; SEQ ID NO: 9; SEQ ID NO: 10; SEQ ID NO: 11. In some embodiments, the antibody further comprises a constant region derived from one or more human antibodies.

In some embodiments, the antibody comprises a heavy chain variable region having the amino acid sequence of: SEQ ID NO: 3, and:
  (i) a light chain variable region having the amino acid sequence of SEQ ID NO: 4;
  (ii) a light chain variable region having the amino acid sequence of SEQ ID NO: 9;
  (iii) a light chain variable region having the amino acid sequence of SEQ ID NO: 10; or
  (iv) a light chain variable region having the amino acid sequence SEQ ID NO: 11.

In some embodiments, the antibody comprises a heavy chain variable region having the amino acid sequence of: SEQ ID NO: 5, and:
  (i) a light chain variable region having the amino acid sequence of SEQ ID NO: 4;
  (ii) a light chain variable region having the amino acid sequence of SEQ ID NO: 9;
  (iii) a light chain variable region having the amino acid sequence of SEQ ID NO: 10; or
  (iv) a light chain variable region having the amino acid sequence SEQ ID NO: 11.

In some embodiments, the antibody comprises a heavy chain variable region having the amino acid sequence of: SEQ ID NO: 6, and:
  (i) a light chain variable region having the amino acid sequence of SEQ ID NO: 4;
  (ii) a light chain variable region having the amino acid sequence of SEQ ID NO: 9;
  (iii) a light chain variable region having the amino acid sequence of SEQ ID NO: 10; or
  (iv) a light chain variable region having the amino acid sequence SEQ ID NO: 11.

In some embodiments, the antibody comprises a heavy chain variable region having the amino acid sequence of: SEQ ID NO: 7, and:
  (i) a light chain variable region having the amino acid sequence of SEQ ID NO: 4;
  (ii) a light chain variable region having the amino acid sequence of SEQ ID NO: 9;
  (iii) a light chain variable region having the amino acid sequence of SEQ ID NO: 10; or
  (iv) a light chain variable region having the amino acid sequence SEQ ID NO: 11.

In some embodiments, the antibody comprises a heavy chain variable region having the amino acid sequence of: SEQ ID NO: 8, and:
  (i) a light chain variable region having the amino acid sequence of SEQ ID NO: 4;
  (ii) a light chain variable region having the amino acid sequence of SEQ ID NO: 9;
  (iii) a light chain variable region having the amino acid sequence of SEQ ID NO: 10; or
  (iv) a light chain variable region having the amino acid sequence SEQ ID NO: 11.

In some preferred embodiments, the antibody comprises:
  (i) a heavy chain variable region having the amino acid sequence of SEQ ID NO: 3, and a light chain variable region having the amino acid sequence of SEQ ID NO: 4;
  (ii) a heavy chain variable region having the amino acid sequence of SEQ ID NO: 3, and a light chain variable region having the amino acid sequence of SEQ ID NO: 10;
  (iii) a heavy chain variable region having the amino acid sequence of SEQ ID NO: 3, and a light chain variable region having the amino acid sequence of SEQ ID NO: 11;
  (iv) a heavy chain variable region having the amino acid sequence of SEQ ID NO: 5, and a light chain variable region having the amino acid sequence of SEQ ID NO: 4;
  (v) a heavy chain variable region having the amino acid sequence of SEQ ID NO: 5, and a light chain variable region having the amino acid sequence of SEQ ID NO: 10;
  (vi) a heavy chain variable region having the amino acid sequence of SEQ ID NO: 5, and a light chain variable region having the amino acid sequence of SEQ ID NO: 11; or
  (vii) a heavy chain variable region having the amino acid sequence of SEQ ID NO: 8, and a light chain variable region having the amino acid sequence of SEQ ID NO: 11.

In some more preferred embodiments, the antibody comprises:
  (i) a heavy chain variable region having the amino acid sequence of SEQ ID NO: 3, and a light chain variable region having the amino acid sequence of SEQ ID NO: 4;
  (ii) a heavy chain variable region having the amino acid sequence of SEQ ID NO: 5 and a light chain variable region having the amino acid sequence of SEQ ID NO: 4; and
  (iii) a heavy chain variable region having the amino acid sequence of SEQ ID NO: 8, and a light chain variable region having the amino acid sequence of SEQ ID NO: 11.

In some particularly preferred embodiments, the antibody comprises a heavy chain variable region having the amino acid sequence of: SEQ ID NO: 3, and a light chain variable region having the amino acid sequence of SEQ ID NO: 4.

In some embodiments, the humanised antibody binds IL13Rα2 with an affinity ($K_D$) no greater than $5 \times 10^{-10}$ M, such as no greater than $2.5 \times 10^{-10}$ M or no greater than $1.5 \times 10^{-10}$ M. In some embodiments, the humanised antibody binds IL13Rα2 with higher affinity ($K_D$) than an antibody comprising a heavy chain variable region having the amino acid sequence of SEQ ID NO: 1 and a light chain variable region having the amino acid sequence of SEQ ID NO: 2, and optionally, an antibody constant region. In some embodiments, affinity ($K_D$) is as determined by a protocol as described in the Examples, for example by Biacore analysis.

In some embodiments, the humanised antibody competitively inhibits the binding to IL13Rα2 of an antibody comprising a heavy chain variable region having the amino acid sequence of SEQ ID NO: 1 and a light chain variable region having the amino acid sequence of SEQ ID NO: 2, and optionally, an antibody constant region.

In some embodiments, the IL13Rα2 is human IL13Rα2.

The sequences of the antibody heavy chain variable regions and/or the light chain variable regions disclosed herein may be modified by, for example, insertions, substitutions and/or deletions to the extent that the humanised antibody maintains the ability to bind to IL13Rα2. The skilled person can ascertain the maintenance of this activity by performing the functional assays described herein, or known in the art.

Accordingly, in some embodiments the heavy chain variable region comprises no more than 20 insertions, substitutions and/or deletions, such as no more than 15, no more than 10, no more than 9, no more than 8, no more than 7, no more than 6, no more than 5, no more than 4, no more than 3, no more than 2, or no more than 1 insertion, substitution and/or deletion. In some embodiments the light chain variable region comprises no more than 20 insertions, substitutions and/or deletions, such as no more than 15, no more than 10, no more than 9, no more than 8, no more than 7, no more than 6, no more than 5, no more than 4, no more than 3, no more than 2, or no more than 1 insertion, substitution and/or deletion.

In some embodiments the humanised antibodies of the disclosure include antibodies comprising VH and VL domains with amino acid sequences that are identical to the sequences described herein.

In a second aspect the present disclosure provides an antibody drug conjugate comprising a humanised antibody according to the first aspect of the disclosure. The conjugates of the disclosure include an antibody conjugated, i.e. covalently attached by a linker, to a drug moiety.

In a third aspect, the present disclosure provides a pharmaceutical composition comprising an antibody according to the first aspect or an antibody drug conjugate according to the second aspect, and a pharmaceutically acceptable diluent, carrier or excipient.

The present disclosure also provides such antibodies, conjugates, and pharmaceutical compositions, for use in a method of treatment, and the use of such antibodies, conjugates, and pharmaceutical compositions in the manufacture of a medicament for use in a method of treatment.

The present disclosure also provides polynucleotides encoding the antibodies of the disclosure, vectors comprising such polynucleotides, and host cells comprising such vectors, as well as methods of producing antibodies of the disclosure comprising culturing such host cells under conditions suitable for the expression of the antibodies of the disclosure.

DETAILED DESCRIPTION

Figure 1:
FIG. 1 Sequence comparison of murine "Clone 47" and "HuCL47" heavy (VH) and light (VK) chain variable domains. CDRs are underlined.

Aspects and embodiments of the present disclosure will now be discussed with reference to the accompanying figures. Further aspects and embodiments will be apparent to those skilled in the art. All documents mentioned in this text are incorporated herein by reference.

Humanised Antibodies

The present disclosure provides humanised anti-IL13Rα2 antibodies.

"Clone 47" is a murine anti-IL13Rα2 antibody described in Balyasnikova et al (J Biol Chem. 2012 Aug. 31; 287(36): 30215-30227). Beginning from the heavy and light chain sequences of murine Clone 47 (SEQ ID NO: 1 and SEQ ID NO: 2 respectively), the present authors have generated a number of humanised heavy and light chain sequences with a view to creating antibodies that have lower immunogenicity in a human individual than chimeric antibodies comprising the heavy and light chain sequences of the murine antibody.

Surprisingly, it was found that certain humanised variants so produced show improved affinity for human IL13Rα2 as compared to the chimeric Clone 47. The humanised antibodies of the disclosure may also possess one or more additional advantageous properties—such as improved stability and/or cell killing activity—as outlined in the following.

Thus, the present disclosure provides an antibody that binds to IL13Rα2, wherein the antibody comprises a heavy chain variable region comprising an amino acid sequence selected from the group consisting of: SEQ ID NO: 3 (VHA; HuCL47 VH); SEQ ID NO: 5 (VHAback); SEQ ID NO: 6 (VHA1); SEQ ID NO: 7 (VHA2); and SEQ ID NO: 8 (VHA3). In some preferred embodiments, the antibody may comprise a heavy chain variable region comprising the amino acid sequence of SEQ ID NO: 3 (VHA; HuCL47 VH).

In some embodiments the antibody may further comprise a light chain variable region comprising an amino acid sequence selected from the group consisting of: SEQ ID NO: 4 (VKA; HuCL47 VL); SEQ ID NO: 9 (VKAback); SEQ ID NO: 10 (VKA1); and SEQ ID NO: 11 (VKA2). In some preferred embodiments, the antibody may comprise a light chain variable region comprising the amino acid sequence of SEQ ID NO: 4 (VKA; HuCL47 VL).

In some embodiments of the disclosure, the antibody may comprise a heavy chain variable region having the amino acid sequence of SEQ ID NO: 3, and a light chain variable region having the amino acid sequence of: SEQ ID NO: 4; SEQ ID NO: 9; SEQ ID NO: 10; or SEQ ID NO: 11.

In some embodiments of the disclosure, the antibody may comprise a heavy chain variable region having the amino acid sequence of SEQ ID NO: 5, and a light chain variable region having the amino acid sequence of: SEQ ID NO: 4; SEQ ID NO: 9; SEQ ID NO: 10; or SEQ ID NO: 11.

In some embodiments of the disclosure, the antibody may comprise a heavy chain variable region having the amino acid sequence of SEQ ID NO: 6, and a light chain variable region having the amino acid sequence of: SEQ ID NO: 4; SEQ ID NO: 9; SEQ ID NO: 10; or SEQ ID NO: 11.

In some embodiments of the disclosure, the antibody may comprise a heavy chain variable region having the amino acid sequence of SEQ ID NO: 7, and a light chain variable region having the amino acid sequence of: SEQ ID NO: 4; SEQ ID NO: 9; SEQ ID NO: 10; or SEQ ID NO: 11.

In some embodiments of the disclosure, the antibody may comprise a heavy chain variable region having the amino acid sequence of SEQ ID NO: 8, and a light chain variable region having the amino acid sequence of: SEQ ID NO: 4; SEQ ID NO: 9; SEQ ID NO: 10; or SEQ ID NO: 11.

Thus, specifically contemplated embodiments of the disclosure include antibodies which may comprise:
i) a heavy chain variable region having the amino acid sequence of SEQ ID NO: 3, and a light chain variable region having the amino acid sequence of SEQ ID NO: 4;
ii) a heavy chain variable region having the amino acid sequence of SEQ ID NO: 3, and a light chain variable region having the amino acid sequence of SEQ ID NO: 9;
iii) a heavy chain variable region having the amino acid sequence of SEQ ID NO: 3, and a light chain variable region having the amino acid sequence of SEQ ID NO: 10;
iv) a heavy chain variable region having the amino acid sequence of SEQ ID NO: 3, and a light chain variable region having the amino acid sequence of SEQ ID NO: 11;
v) a heavy chain variable region having the amino acid sequence of SEQ ID NO: 5, and a light chain variable region having the amino acid sequence of SEQ ID NO: 4;
vi) a heavy chain variable region having the amino acid sequence of SEQ ID NO: 5, and a light chain variable region having the amino acid sequence of SEQ ID NO: 9;
vii) a heavy chain variable region having the amino acid sequence of SEQ ID NO: 5, and a light chain variable region having the amino acid sequence of SEQ ID NO: 10;
viii) a heavy chain variable region having the amino acid sequence of SEQ ID NO: 5, and a light chain variable region having the amino acid sequence of SEQ ID NO: 11;
ix) a heavy chain variable region having the amino acid sequence of SEQ ID NO: 6, and a light chain variable region having the amino acid sequence of SEQ ID NO: 4;
x) a heavy chain variable region having the amino acid sequence of SEQ ID NO: 6, and a light chain variable region having the amino acid sequence of SEQ ID NO: 9;
xi) a heavy chain variable region having the amino acid sequence of SEQ ID NO: 6, and a light chain variable region having the amino acid sequence of SEQ ID NO: 10;
xii) a heavy chain variable region having the amino acid sequence of SEQ ID NO: 6, and a light chain variable region having the amino acid sequence of SEQ ID NO: 11;
xiii) a heavy chain variable region having the amino acid sequence of SEQ ID NO: 7, and a light chain variable region having the amino acid sequence of SEQ ID NO: 4;
xiv) a heavy chain variable region having the amino acid sequence of SEQ ID NO: 7, and a light chain variable region having the amino acid sequence of SEQ ID NO: 9;
xv) a heavy chain variable region having the amino acid sequence of SEQ ID NO: 7, and a light chain variable region having the amino acid sequence of SEQ ID NO: 10;
xvi) a heavy chain variable region having the amino acid sequence of SEQ ID NO: 7, and a light chain variable region having the amino acid sequence of SEQ ID NO: 11;
xvii) a heavy chain variable region having the amino acid sequence of SEQ ID NO: 8, and a light chain variable region having the amino acid sequence of SEQ ID NO: 4;
xviii) a heavy chain variable region having the amino acid sequence of SEQ ID NO: 8, and a light chain variable region having the amino acid sequence of SEQ ID NO: 9;
xix) a heavy chain variable region having the amino acid sequence of SEQ ID NO: 8, and a light chain variable region having the amino acid sequence of SEQ ID NO: 10; and
xx) a heavy chain variable region having the amino acid sequence of SEQ ID NO: 8, and a light chain variable region having the amino acid sequence of SEQ ID NO: 11.

Some preferred specifically contemplated embodiments of the disclosure include antibodies which comprise:
a heavy chain variable region having the amino acid sequence of SEQ ID NO: 3 (VHA; HuCL47 VH), and a light chain variable region having the amino acid sequence of SEQ ID NO: 4 (VKA; HuCL47 VL);
a heavy chain variable region having the amino acid sequence of SEQ ID NO: 3 (VHA; HuCL47 VH), and a light chain variable region having the amino acid sequence of SEQ ID NO: 10 (VKA1);
a heavy chain variable region having the amino acid sequence of SEQ ID NO: 3 (VHA; HuCL47 VH), and a light chain variable region having the amino acid sequence of SEQ ID NO: 11 (VKA2);
a heavy chain variable region having the amino acid sequence of SEQ ID NO: 5 (VHAback), and a light chain variable region having the amino acid sequence of SEQ ID NO: 4 (VKA; HuCL47 VL);
a heavy chain variable region having the amino acid sequence of SEQ ID NO: 5 (VHAback), and a light chain variable region having the amino acid sequence of SEQ ID NO: 10 (VKA1);
a heavy chain variable region having the amino acid sequence of SEQ ID NO: 5 (VHAback), and a light chain variable region having the amino acid sequence of SEQ ID NO: 11 (VKA2); and
a heavy chain variable region having the amino acid sequence of SEQ ID NO: 8 (VHA3), and a light chain variable region having the amino acid sequence of SEQ ID NO: 11 (VKA2).

Other preferred embodiments of the disclosure include antibodies which comprise:
a heavy chain variable region having the amino acid sequence of SEQ ID NO: 3 (VHA; HuCL47 VH), and a light chain variable region having the amino acid sequence of SEQ ID NO: 4 (VKA; HuCL47 VL);
a heavy chain variable region having the amino acid sequence of SEQ ID NO: 5 (VHAback), and a light chain variable region having the amino acid sequence of SEQ ID NO: 4 (VKA; HuCL47 VL); and
a heavy chain variable region having the amino acid sequence of SEQ ID NO: 8 (VHA3), and a light chain variable region having the amino acid sequence of SEQ ID NO: 11 (VKA2).

In some particularly preferred embodiments of the disclosure the antibody comprises a heavy chain variable region having the amino acid sequence of: SEQ ID NO: 3, and a light chain variable region having the amino acid sequence of SEQ ID NO: 4. Such antibodies may be referred to herein as "huCL47".

The antibodies of the disclosure are humanised or fully human antibodies, or comprise variable domains that are humanised or fully human. The antibodies of the disclosure may be isolated humanised or fully human antibodies. In some embodiments, the antibodies of the disclosure may further comprise an antibody constant region derived from one or more human antibodies.

In one embodiment, the present invention provides an antibody that binds to Interleukin-13 receptor subunit alpha-2 (IL13Rα2), comprising a heavy chain comprising the complementarity determining regions (CDRs) shown in SEQ ID NO:13, SEQ ID NO: 14 and SEQ ID: NO 15; and/or a light chain comprising (i) the CDRs shown in SEQ ID NO:16, SEQ ID NO: 17 and SEQ ID: NO 18; and (ii) a serine residue at position 30 (numbering with reference to SEQ ID NO: 3) wherein at least the variable regions are fully human. In one embodiment the antibody is fully human, including the constant regions. In a related embodiment the present invention provides an antibody conjugate comprising said antibody and pyrollobenzodiazepine dimer. In one embodiment the light chain is a human kappa light chain.

Antigen Binding

The antibodies described herein are antibodies which specifically bind to IL13Rα2.

As used herein, "bind to IL13Rα2" and "binds IL13Rα2" are used to mean the antibody binds IL13Rα2 with a higher affinity than a non-specific partner such as Bovine Serum Albumin (BSA, Genbank accession no. CAA76847, version no. CAA76847.1 GI:3336842, record update date: Jan. 7, 2011 02:30 PM). In some embodiments the antibody binds IL13Rα2 with an association constant (Ka) at least 2, 3, 4, 5, 10, 20, 50, 100, 200, 500, 1000, 2000, 5000, 104, 105 or 106-fold higher than the antibody's association constant for BSA, when measured at physiological conditions.

In some embodiments, the IL13Rα2 polypeptide corresponds to the amino acid sequence disclosed at UniProt accession no: Q14627 (entry version 190) or a fragment thereof. In some embodiments, the IL13Rα2 polypeptide corresponds to an amino acid sequence having at least 70%, 80%, 90%, 95%, 99% or 100% sequence identity with the full-length of the amino acid sequence disclosed at UniProt accession no: Q14627 (entry version 190) or a fragment thereof. In some embodiments, the IL13Rα2 polypeptide has the sequence of SEQ ID NO: 12.

Antibody Affinity

Surprisingly, the present authors have found that the process of humanisation increases the affinity of the humanised antibodies for human IL13Rα2 as compared to the chimeric (Ch) Clone 47, as determined in a Biacore binding assay (see Example 2).

Thus, the antibodies of the invention can bind IL13Rα2 with high affinity. For example, in some embodiments the humanised antibodies of the disclosure may bind IL13Rα2 with dissociation constant ($K_D$) no greater than $10^{-6}$ M, no greater than $5 \times 10^{-6}$ M, no greater than $10^{-7}$ M, no greater than $5 \times 10^{-7}$ M, no greater than $10^{-8}$ M, no greater than $5 \times 10^{-8}$ M, no greater than $10^{-9}$ M, no greater than $5 \times 10^{-9}$ M, no greater than $10^{-10}$ M, no greater than $5 \times 10^{-10}$ M, no greater than $10^{-11}$ M, no greater than $5 \times 10^{-11}$ M, no greater than $10^{-12}$ M, no greater than $5 \times 10^{-12}$ M, no greater than $10^{-13}$ M, no greater than $5 \times 10^{-13}$ M, no greater than $10^{-14}$ M, no greater than $5 \times 10^{-14}$ M, no greater than $10^{-15}$ M, or no greater than $5 \times 10^{-15}$ M.

In some embodiments the humanised antibodies of the disclosure may bind IL13Rα2 with dissociation constant ($K_D$) no greater than 0.52, 0.51, 0.50, 0.49, 0.48, 0.47, 0.46, 0.45, 0.44, 0.43, 0.42, 0.41, or 0.40 nM. In some embodiments, the humanised antibodies of the disclosure may bind IL13Rα2 with dissociation constant ($K_D$) no greater than 0.40, 0.35, 0.30, 0.25, 0.20, 0.15, or no greater than 0.10 nM.

In some embodiments, the humanised antibodies of the disclosure may bind IL13Rα2 with dissociation constant ($K_D$) from $10^{-8}$ M to $10^{-10}$ M, from $10^{-10}$ M to $10^{-12}$ M, from $10^{-12}$ M to $10^{-14}$ M, or from $10^{-14}$ M to $10^{-16}$ M. In some embodiments, the humanised antibodies of the disclosure may bind IL13Rα2 with dissociation constant ($K_D$) from $5 \times 10^{-10}$ to $5 \times 10^{-11}$ M.

Suitable methods for determining antibody affinity will be well known to the skilled person—for example enzyme-linked immunosorbent assay (ELISA) and surface plasmon resonance (SPR) techniques. In some embodiments, the $K_D$ may be determined and calculated by the methods described in the Examples.

In some embodiments the humanised antibodies may competitively inhibit the in vivo and/or in vitro binding to human IL13Rα2 of the murine "Clone 47" antibody. In some embodiments, humanised antibodies may competitively inhibit the in vivo and/or in vitro binding to human IL13Rα2 of an antibody comprising a heavy chain variable region having the amino acid sequence of SEQ ID NO: 1 and a light chain variable region having the amino acid sequence of SEQ ID NO: 2.

In some embodiments an equimolar dose of the humanised antibodies of the disclosure may competitively inhibit at least 20% of the binding the murine "Clone 47" antibody, such as at least 30%, at least 40%, at least 50%, at least 60%, at least 70%, at least 80%, or at least 90% of the binding. Percentage binding may be measured by, for example, a competitive ELISA assay where % inhibition of binding is calculated as [(1−absorbance of test sample)/(absorbance of negative control)].

In some embodiments the humanised antibodies of the disclosure may have a higher affinity for a human IL13Rα2 antigen than the murine "Clone 47" antibody. In some embodiments the humanised antibodies of the disclosure may have a higher affinity for a human IL13Rα2 antigen than an antibody comprising a heavy chain variable region having the amino acid sequence of SEQ ID NO: 1 and a light chain variable region having the amino acid sequence of SEQ ID NO: 2.

In some embodiments the $K_D$ of the humanized antibody with the human IL13Rα2 antigen will be no more than 0.9 of the $K_D$ of the murine "Clone 47" antibody/an antibody comprising a heavy chain variable region having the amino acid sequence of SEQ ID NO: 1 and a light chain variable region having the amino acid sequence of SEQ ID NO: 2. For example the $K_D$ of the humanized antibody with the human IL13Rα2 antigen may be no more than 0.8, 0.7, 0.6, 0.5, 0.4, 0.3, 0.2, 0.1, 0.05, 0.01, or 0.001 of the $K_D$ of one or more of the antibodies described above. In some preferred embodiments, the $K_D$ may be no more than 0.5, or no more than 0.2 of the $K_D$ of one or more of the antibodies described above.

Antibody Isoelectric Point (PI)

A molecule carries no net charge when the pH of its surroundings equals the molecules pI. The net charge of a molecule affects the solubility of the molecule, with biological molecules such as proteins typically having minimum solubility in water or salt solutions at the pH that corresponds to their pI. Thus, proteins whose pI is 7.35-7.45 are at their minimum solubility in human blood, whose pH is typically in the range 7.35-7.45.

When the pH of its surroundings is below the protein's pI, then the molecule carries a net positive charge. When the pH of its surroundings is above the protein's pI, then the molecule carries a net negative charge. In general, higher net positive charge of an antibody results in increased tissue retention and blood clearance with shorter half-life, while lower pI/lower net positive charge results in decreased tissue retention and longer half-life (Boswell et al, Bioconjug Chem. 2010 Dec. 15; 21(12):2153-63).

In some embodiments the humanised antibodies of the disclosure may have a pI less than the murine "Clone 47" antibody. In some embodiments the humanised antibodies of the disclosure may have a pI less than an antibody comprising a heavy chain variable region having the amino acid sequence of SEQ ID NO: 1 and a light chain variable region having the amino acid sequence of SEQ ID NO: 2. In some embodiments the humanised antibodies of the disclosure may have a pI of no more than 9.0, such as no more than 8.5, no more than 8.0, or no more than 7.5. In some embodiments the humanised antibodies of the disclosure may have a pI of no more than 8.9, 8.8, 8.7, 8.6, 8.5, 8.4, 8.3, 8.2, or 8.1. In some embodiments the humanised antibodies of the disclosure may have a pI of no more than 7.9, 7.8, or 7.7.

In some embodiments the humanised antibodies of the disclosure may have a pI greater than the murine "Clone 47" antibody. In some embodiments the humanised antibodies of the disclosure may have a pI greater than an antibody comprising a heavy chain variable region having the amino acid sequence of SEQ ID NO: 1 and a light chain variable region having the amino acid sequence of SEQ ID NO: 2. In some embodiments the humanised antibodies of the disclosure may have a pI of at least 7.5, such as at least 8.0, at least 8.5, or at least 9.0. In some embodiments the humanised antibodies of the disclosure may have a pI of at least 7.5, 7.6, 7.7, 7.8, 7.9, or 8.0. In some preferred embodiments the humanised antibodies of the disclosure may have a pI of at least 7.6. In some preferred embodiments the humanised antibodies of the disclosure may have a pI of at least 7.63.

Antibody Stability

Surprisingly, the present authors have found that the process of humanisation may increase the stability of the humanised antibodies, as determined by binding to IL13Rα2 following incubation at 4° C. or 45° C. for 8 days as assessed by ELISA (see Example 2).

Thus, the antibodies of the disclosure may have improved stability properties as compared to a non-humanised anti-IL13Rα2 antibody or other humanised anti-IL13Rα2 antibodies. In some embodiments, the humanised antibodies may have improved stability properties as compared an antibody comprising a heavy chain variable region having the amino acid sequence of SEQ ID NO: 1 and a light chain variable region having the amino acid sequence of SEQ ID NO: 2.

Suitable means for assessing stability properties are well known to the skilled person—for example, protein thermal shift and temperature stability assays. In some embodiments, stability properties of the humanised antibodies of the disclosure may be determined by one or more of the methods described in the Examples. In some embodiments, stability properties of the humanised antibodies of the disclosure may be determined by binding to IL13Rα2 following incubation at 4° C. or 45° C. for 8 days, as assessed by ELISA.

In some embodiments, the humanised antibodies of the disclosure may exhibit less than a 5, 10, 15, 20, 25, 30, 35, 40, 45, or 50% decrease in binding affinity to IL13Rα2 following incubation at 45° C. for 8 days. In some embodiments, the humanised antibodies of the disclosure may exhibit less than a 4 fold reduction, for example, less than 3.5 fold, less than 3 fold, less than 2.5 fold, less than 2 fold, or less than 1.5 fold reduction in binding affinity to L13Rα2 following incubation at 45° C. for 8 days.

Cell Killing Activity/Cytotoxicity

In some cases the humanised antibodies of the disclosure and/or antibody-drug conjugates comprising the humanised antibodies of the disclosure may have high cell killing activity—for example, as determined by EC50 values.

In some embodiments the humanised antibodies and/or antibody-drug conjugates of the disclosure may have an EC50 that is lower than the murine "Clone 47" antibody or an antibody-drug conjugate comprising the murine "Clone 47" antibody. In some embodiments the humanised antibodies and/or antibody-drug conjugates of the disclosure may have an EC50 that is lower than an antibody or antibody-drug conjugate comprising a heavy chain variable region having the amino acid sequence of SEQ ID NO: 1 and a light chain variable region having the amino acid sequence of SEQ ID NO: 2. In some embodiments the humanised antibodies and/or antibody-drug conjugates of the disclosure may have an EC50 that is at least 10, 20, 30, 40, 50, 60, 70, 80, 90, or 100% lower than that of one or more of the antibodies/conjugates described above. Suitable means for determining cell killing activity/cytotoxicity and EC50 values are well known to the skilled person. In some embodiments, these may be determined by the methods described in the Examples.

Inhibition of Tumour Growth

In some cases the humanised antibodies of the disclosure and/or antibody-drug conjugates comprising the humanised antibodies of the disclosure may arrest or reduce the rate of growth of IL13Rα2-expressing tumours.

In some embodiments the humanised antibodies of the disclosure may inhibit tumour growth by at least 10% compared to a control tumour. That is, the volume of the antibody treated tumour is no more than 90% of the volume of the control tumour. For example, in some embodiments the antibodies of the disclosure may inhibit tumour growth by at least 20% compared to a control tumour, such as at least 30%, at least 40%, at least 50%, at least 60%, at least 70%, at least 80%, or at least 90%.

In some embodiments, the tumour inhibitory effect of the humanised antibodies of the disclosure may be greater than that of the murine "Clone 47" antibody or an antibody-drug conjugate comprising the murine "Clone 47" antibody. In some embodiments, the tumour inhibitory effect of the humanised antibodies of the disclosure may be greater than that of an antibody or antibody-drug conjugate comprising a heavy chain variable region having the amino acid sequence of SEQ ID NO: 1 and a light chain variable region having the amino acid sequence of SEQ ID NO: 2.

In some embodiments the tumour inhibitory effect of the humanised antibodies of the disclosure may be greater than that of one or more of the antibodies described above. In some embodiments the tumour inhibitory effect of the humanised antibodies of the disclosure may be at least 10, 20, 30, 40, 50, 60, 70, 80, 90, or 100% higher than that of one or more of the antibodies described above. Suitable means for determining the effects of the humanised antibodies of the disclosure on tumour growth are well known to the skilled person.

Antibody Immunogenicity

The humanised antibodies of the disclosure have reduced immunogenicity in a human subject as compared to a non-humanised antibody of the same specificity (for example, a mouse antibody precursor prior to humanisation). In some embodiments the humanised antibodies of the disclosure may have immunogenicity in a human subject lower than an otherwise identical antibody or antibody fragment comprising a heavy chain variable region having the amino acid sequence of SEQ ID NO: 1 and a light chain variable region having the amino acid sequence of SEQ ID NO: 2.

Low or reduced immunogenicity can be characterized by the ability to treat patients for extended periods with measurable alleviation of symptoms and low and/or acceptable toxicity. Low or acceptable immunogenicity and/or high affinity, as well as other suitable properties, can contribute to the therapeutic results achieved. "Reduced immunogenicity" is defined herein as raising significant HAHA, HACA or HAMA responses in less 90%, such as less than 80%, less than 70%, less than 60%, less than 50%, less than 40%, less than 30%, less than 20%, less than 10% of the proportion of patients who show a significant HAHA, HACA or HAMA response when treated with the antibodies described above.

Antibody Production

The present disclosure also provides methods and means of producing the humanised antibodies of the disclosure.

Accordingly, in another aspect the disclosure provides nucleic acid molecules encoding the humanised antibodies, along with nucleic acid molecules complementary to nucleic acid molecules encoding the humanised antibodies.

In another aspect, the disclosure provides a pharmaceutical composition comprising an antibody of the disclosure, optionally further comprising a pharmaceutically acceptable carrier or excipient.

In another aspect the disclosure provides a vector, such as an expression vector, comprising a nucleic acid of the disclosure.

In another aspect, the disclosure provides host cells transfected with a vector of the disclosure. The host cells may be prokaryotic or eukaryotic. For example, the cells may be bacterial, fungal, insect, or mammalian (such as mouse, primate or human).

In another aspect the disclosure provides a method of making the antibodies by culturing the host cells of the disclosure.

In some cases, when expressed in a host cell of the disclosure, the humanised antibodies of the disclosure may be expressed at a higher level, or with higher productivity or yield, as compared to a non-humanised anti-IL13Rα2 antibody or other humanised anti-IL13Rα2 antibodies.

In some embodiments the humanised antibodies of the disclosure may be expressed at a higher level, or with higher productivity or yield, than an antibody comprising a heavy chain variable region having the amino acid sequence of SEQ ID NO: 1 and a light chain variable region having the amino acid sequence of SEQ ID NO: 2. In some embodiments the humanised antibodies of the disclosure may be expressed at a higher level, or with higher productivity or yield, than an antibody comprising a heavy chain variable region having the amino acid sequence of SEQ ID NO: 3 (VHA) and a light chain variable region having the amino acid sequence of SEQ ID NO: 9 (VKAback);

a heavy chain variable region having the amino acid sequence of SEQ ID NO: 5 (VHAback) and a light chain variable region having the amino acid sequence of SEQ ID NO: 9 (VKAback);

a heavy chain variable region having the amino acid sequence of SEQ ID NO: 6 (VHA1) and a light chain variable region having the amino acid sequence of SEQ ID NO: 4 (VKA);

a heavy chain variable region having the amino acid sequence of SEQ ID NO: 6 (VHA1) and a light chain variable region having the amino acid sequence of SEQ ID NO: 9 (VKAback);

a heavy chain variable region having the amino acid sequence of SEQ ID NO: 6 (VHA1) and a light chain variable region having the amino acid sequence of SEQ ID NO: 10 (VKA1);

a heavy chain variable region having the amino acid sequence of SEQ ID NO: 6 (VHA1) and a light chain variable region having the amino acid sequence of SEQ ID NO: 11 (VKA2);

a heavy chain variable region having the amino acid sequence of SEQ ID NO: 7 (VHA2) and a light chain variable region having the amino acid sequence of SEQ ID NO: 4 (VKA);

a heavy chain variable region having the amino acid sequence of SEQ ID NO: 7 (VHA2) and a light chain variable region having the amino acid sequence of SEQ ID NO: 9 (VKAback);

a heavy chain variable region having the amino acid sequence of SEQ ID NO: 7 (VHA2) and a light chain variable region having the amino acid sequence of SEQ ID NO: 10 (VKA1);

a heavy chain variable region having the amino acid sequence of SEQ ID NO: 7 (VHA2) and a light chain variable region having the amino acid sequence of SEQ ID NO: 11 (VKA2);

a heavy chain variable region having the amino acid sequence of SEQ ID NO: 8 (VHA3) and a light chain variable region having the amino acid sequence of SEQ ID NO: 4 (VKA);

a heavy chain variable region having the amino acid sequence of SEQ ID NO: 8 (VHA3) and a light chain variable region having the amino acid sequence of SEQ ID NO: 9 (VKAback); and a heavy chain variable region having the amino acid sequence of SEQ ID NO: 8 (VHA3) and a light chain variable region having the amino acid sequence of SEQ ID NO: 10 (VKA1).

In some embodiments the humanised antibodies of the disclosure may be expressed at a higher level, or with higher productivity or yield, than one or more of the antibodies described above when expressed in the same host cell type and cultured under the same conditions. In some embodiments the level of expression or productivity or yield may be at least 10, 20, 30, 40, 50, 60, 70, 80, 90, or 100% higher than one or more of the antibodies described above when expressed in the same host cell type and cultured under the same conditions. In some embodiments the level of expression or productivity or yield may be at least 110, 120, 130, 140, 150, 160, 170, 180, 190, or 200% higher than one or more of the antibodies described above when expressed in the same host cell type and cultured under the same conditions. Suitable means for determining the level of expression of recombinant proteins are well known to the skilled person, for example, ELISA and Western Blot techniques. In some embodiments, the level of expression/productivity/yield may be determined by the methods described in the Examples.

In some cases, when expressed in a host cell of the disclosure, the humanised antibodies of the disclosure may have a lower level of aggregation or fragmentation, as compared to a non-humanised anti-IL13Rα2 antibody or other humanised anti-IL13Rα2 antibodies. In some embodiments the humanised antibodies of the disclosure may have a lower level of aggregation or fragmentation than an antibody comprising a heavy chain variable region having the amino acid sequence of SEQ ID NO: 1 and a light chain variable region having the amino acid sequence of SEQ ID NO: 2. In some embodiments the humanised antibodies of the disclosure may have a lower level of aggregation or fragmentation than a non-humanised anti-IL13Rα2 antibody or other humanised anti-IL13Rα2 antibodies when expressed in the same host cell type and cultured under the same conditions. In some embodiments the level of aggregation or fragmentation may be at least 10, 20, 30, 40, 50, 60, 70, 80, 90, or 100% lower when expressed in the same host cell type and cultured under the same conditions. In some embodiments the level of aggregation or fragmentation may be at least 110, 120, 130, 140, 150, 160, 170, 180, 190, or 200% lower when expressed in the same host cell type and cultured under the same conditions. Suitable means for determining aggregation or fragmentation of recombinant proteins are well known to the skilled person, for example, size exclusion chromatography (SEC). In some embodiments, the level of aggregation or fragmentation may be determined by the methods described in the Examples.

Definitions

Antibody

The term "antibody" herein is used in the broadest sense and specifically covers monoclonal antibodies, polyclonal antibodies, dimers, multimers, multispecific antibodies (e.g., bispecific antibodies), intact antibodies and antibody fragments, so long as they exhibit the desired biological activity, for example, the ability to bind IL13Rα2. Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass, or allotype (e.g. human G1 m1, G1 m2, G1 m3, non-G1 m1 [that, is any allotype other than G1m1], G1m17, G2m23, G3m21, G3m28, G3m11, G3m5, G3m13, G3m14, G3m10, G3m15, G3m16, G3m6, G3m24, G3m26, G3m27, A2m1, A2m2, Km1, Km2 and Km3) of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', F(ab')$_2$, and scFv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (see, U.S. Pat. No. 4,816,567). The monoclonal antibodies may also be isolated from phage antibody libraries using the techniques described in Clackson et al. (1991) Nature, 352:624-628; Marks et al. (1991) J. Mol. Biol., 222:581-597 or from transgenic mice carrying a fully human immunoglobulin system (Lonberg (2008) Curr. Opinion 20(4):450-459).

Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Nat. Acad. Sci. USA, 81:6851-6855). Chimeric antibodies include "primatized" antibodies comprising variable domain antigen-binding sequences derived from a non-human primate (e.g. Old World Monkey or Ape) and human constant region sequences.

An "intact antibody" herein is one comprising VL and VH domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

Humanized

As used herein "humanized" antibodies include any combination of the herein described anti-IL13Rα2 antibodies. In these antibodies framework residues from the chimeric MSAb-1 and X09.2 antibodies have been largely replaced with the corresponding residues from human immunoglobulins. As many of the human amino acid residues as possible are retained, but critical human residues may be modified as necessary to support the antigen binding site formed by the CDRs and recapitulate the antigen binding potency of the chimeric antibodies. Such changes or variations optionally and preferably retain or reduce the immunogenicity in humans or other primate species relative to non-modified antibodies.

A "humanized antibody" refers to a polypeptide comprising at least a portion of a modified variable region of a human antibody wherein a portion of the variable region, preferably a portion substantially less than the intact human variable domain, has been substituted by the corresponding sequence from a non-human species and wherein the modified variable region is linked to at least another part of another protein, preferably the constant region of a human antibody. The expression "humanized antibodies" includes human antibodies in which one or more complementarity determining region ("CDR") amino acid residues and/or one or more framework region ("FW" or "FR") amino acid residues are substituted by amino acid residues from analogous sites in rodent or other non-human antibodies. The expression "humanized antibody" also includes an immunoglobulin amino acid sequence variant or fragment thereof that comprises an FR having substantially the amino acid sequence of a human immunoglobulin and a CDR having substantially the amino acid sequence of a non-human immunoglobulin.

"Humanized" forms of non-human (e.g., murine) antibodies are chimeric antibodies that contain minimal sequence derived from non-human immunoglobulin. Or, looked at another way, a humanized antibody is a human antibody that also contains selected sequences from non-human (e.g. murine) antibodies in place of the human sequences. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins.

There are a range of humanisation techniques, including 'CDR grafting', 'guided selection', 'deimmunization', 'resurfacing' (also known as 'veneering'), 'composite antibodies', 'Human String Content Optimisation' and framework shuffling.

CDR Grafting

In this technique, the humanized antibodies are human immunoglobulins (recipient antibody) in which residues from a complementary-determining region (CDR) of the recipient antibody are replaced by residues from a CDR of a non-human species (donor antibody) such as mouse, rat, camel, bovine, goat, or rabbit having the desired properties (in effect, the non-human CDRs are 'grafted' onto the human framework). In some instances, framework region (FR) residues of the human immunoglobulin are replaced by corresponding non-human residues (this may happen when, for example, a particular FR residue has significant effect on antigen binding).

Furthermore, humanized antibodies can comprise residues that are found neither in the recipient antibody nor in the imported CDR or framework sequences. These modifications are made to further refine and maximize antibody performance. Thus, in general, a humanized antibody will comprise all of at least one, and in one aspect two, variable domains, in which all or all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin.

Guided Selection

The method consists of combining the $V_H$ or $V_L$ domain of a given non-human antibody specific for a particular epitope with a human $V_H$ or $V_L$ library and specific human V domains are selected against the antigen of interest. This selected human VH is then combined with a VL library to generate a completely human VH×VL combination. The method is described in Nature Biotechnology (N.Y.) 12, (1994) 899-903.

Composite Antibodies

In this method, two or more segments of amino acid sequence from a human antibody are combined within the final antibody molecule. They are constructed by combining multiple human VH and VL sequence segments in combinations which limit or avoid human T cell epitopes in the final composite antibody V regions. Where required, T cell epitopes are limited or avoided by, exchanging V region segments contributing to or encoding a T cell epitope with alternative segments which avoid T cell epitopes. This method is described in US 2008/0206239 A1.

Deimmunization

This method involves the removal of human (or other second species) T-cell epitopes from the V regions of the therapeutic antibody (or other molecule). The therapeutic antibodies V-region sequence is analysed for the presence of MHC class II-binding motifs by, for example, comparison with databases of MHC-binding motifs (such as the "motifs" database hosted at wehi.edu.au). Alternatively, MHC class II-binding motifs may be identified using computational threading methods such as those devised by Altuvia et al. (J. Mol. Biol. 249 244-250 (1995)); in these methods, consecutive overlapping peptides from the V-region sequences are testing for their binding energies to MHC class II proteins. This data can then be combined with information on other sequence features which relate to successfully presented peptides, such as amphipathicity, Rothbard motifs, and cleavage sites for cathepsin B and other processing enzymes.

Once potential second species (e.g. human) T-cell epitopes have been identified, they are eliminated by the alteration of one or more amino acids. The modified amino acids are usually within the T-cell epitope itself, but may also be adjacent to the epitope in terms of the primary or secondary structure of the protein (and therefore, may not be adjacent in the primary structure). Most typically, the alteration is by way of substitution but, in some circumstances amino acid addition or deletion will be more appropriate.

All alterations can be accomplished by recombinant DNA technology, so that the final molecule may be prepared by expression from a recombinant host using well established methods such as Site Directed Mutagenesis. However, the use of protein chemistry or any other means of molecular alteration is also possible.

Resurfacing

This method involves:
(a) determining the conformational structure of the variable region of the non-human (e.g. rodent) antibody (or fragment thereof) by constructing a three-dimensional model of the non-human antibody variable region;
(b) generating sequence alignments using relative accessibility distributions from x-ray crystallographic structures of a sufficient number of non-human and human antibody variable region heavy and light chains to give a set of heavy and light chain framework positions wherein the alignment positions are identical in 98% of the sufficient number of non-human antibody heavy and light chains;
(c) defining for the non-human antibody to be humanized, a set of heavy and light chain surface exposed amino acid residues using the set of framework positions generated in step (b);
(d) identifying from human antibody amino acid sequences a set of heavy and light chain surface exposed amino acid residues that is most closely identical to the set of surface exposed amino acid residues defined in step (c), wherein the heavy and light chain from the human antibody are or are not naturally paired;
(e) substituting, in the amino acid sequence of the non-human antibody to be humanized, the set of heavy and light chain surface exposed amino acid residues defined in step (c) with the set of heavy and light chain surface exposed amino acid residues identified in step (d);
(f) constructing a three-dimensional model of the variable region of the non-human antibody resulting from the substituting specified in step (e);
(g) identifying, by comparing the three-dimensional models constructed in steps (a) and (f), any amino acid residues from the sets identified in steps (c) or (d), that are within 5 Angstroms of any atom of any residue of the complementarity determining regions of the non-human antibody to be humanized; and
(h) changing any residues identified in step (g) from the human to the original non-human amino acid residue to thereby define a non-human antibody humanizing set of surface exposed amino acid residues; with the proviso that step (a) need not be conducted first, but must be conducted prior to step (g).

Superhumanization

The method compares the non-human sequence with the functional human germline gene repertoire. Those human genes encoding canonical structures identical or closely related to the non-human sequences are selected. Those selected human genes with highest homology within the CDRs are chosen as FR donors. Finally, the non-human CDRs are grafted onto these human FRs. This method is described in patent WO 2005/079479 A2.

Human String Content Optimization

This method compares the non-human (e.g. mouse) sequence with the repertoire of human germline genes and the differences are scored as Human String Content (HSC) that quantifies a sequence at the level of potential MHC/T-cell epitopes. The target sequence is then humanized by maximizing its HSC rather than using a global identity measure to generate multiple diverse humanized variants (described in Molecular Immunology, 44, (2007) 1986-1998).

Framework Shuffling

The CDRs of the non-human antibody are fused in-frame to cDNA pools encompassing all known heavy and light chain human germline gene frameworks. Humanised antibodies are then selected by e.g. panning of the phage displayed antibody library. This is described in Methods 36, 43-60 (2005).

Sequence Modifications

The sequences of the antibody heavy chain variable regions and/or the light chain variable regions disclosed herein may be modified by substitution, insertion or deletion. Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Preferred conservative substitutions are those wherein one amino acid is substituted for another within the groups of amino acids indicated herein below:

Amino acids having polar side chains (Asp, Glu, Lys, Arg, His, Asn, Gin, Ser, Thr, Tyr, and Cys)
Amino acids having non-polar side chains (Gly, Ala, Val, Leu, lie, Phe, Trp, Pro, and Met)
Amino acids having aliphatic side chains (Gly, Ala Val, Leu, lie)
Amino acids having cyclic side chains (Phe, Tyr, Trp, His, Pro)
Amino acids having aromatic side chains (Phe, Tyr, Trp)
Amino acids having acidic side chains (Asp, Glu)
Amino acids having basic side chains (Lys, Arg, His)
Amino acids having amide side chains (Asn, Gln)
Amino acids having hydroxy side chains (Ser, Thr)
Amino acids having sulphur-containing side chains (Cys, Met),
Neutral, weakly hydrophobic amino acids (Pro, Ala, Gly, Ser, Thr)
Hydrophilic, acidic amino acids (Gin, Asn, Glu, Asp), and
Hydrophobic amino acids (Leu, lie, Val)

Particular preferred conservative amino acids substitution groups are: Val-Leu-Ile, Phe-Tyr, Lys-Arg, Ala-Val, and Asn-Gln.

In some embodiments, the antibodies of the disclosure may comprise a heavy chain having an amino acid sequence with 80% or more amino acid sequence identity (for example, about 85% or more, 86% or more, 87% or more, 88% or more, 89% or more, 90% or more, 91% or more, 92% or more, 93% or more, 94% or more, 95% or more, 96% or more, 97% or more, 98% or more, 99% or more sequence identity) to a heavy chain described herein. In some embodiments, the antibodies of the disclosure may comprise a light chain having an amino acid sequence with 80% or more amino acid sequence identity (for example, about 85% or more, 86% or more, 87% or more, 88% or more, 89% or more, 90% or more, 91% or more, 92% or more, 93% or more, 94% or more, 95% or more, 96% or more, 97% or more, 98% or more, 99% or more sequence identity) to a light chain described herein.

In some embodiments, the antibodies of the disclosure may comprise a heavy chain having an amino acid sequence identical to the amino acid sequence of a heavy chain described herein, except that it includes 1, 2, 3, 4, 5, 6, 7, 8, 9 or 10 amino acid modifications (e.g., substitutions, insertions and/or deletions) relative to the amino acid sequence of the heavy chain described herein. In some embodiments, the antibodies of the disclosure may comprise a light chain having an amino acid sequence identical to the amino acid sequence of a light chain described herein, except that it includes 1, 2, 3, 4, 5, 6, 7, 8, 9 or 10 amino acid modifications (e.g., substitutions, insertions and/or deletions) relative to the amino acid sequence of the light chain described herein.

Antibody Production

Humanized antibodies, fragments and regions can be produced by cloning DNA segments encoding the H and L chain antigen-binding regions of the anti-IL13Rα2 antibody, and joining these DNA segments to DNA segments including CH and CL regions, respectively, to produce full length immunoglobulin-encoding genes.

For full-length antibody molecules, the immunoglobulin cDNAs can be obtained from mRNA of hybridoma cell lines. Antibody heavy and light chains are cloned in a mammalian expression vector system. Assembly is documented with DNA sequence analysis. The antibody construct can be expressed in human or other mammalian host cell lines. The construct can be validated by transient transfection assays and immunoassay of the expressed antibody. Stable cell lines with the highest productivity can be isolated and screened using rapid assay methods.

Methods of Treatment

The antibodies and conjugates of the present disclosure may be used in a method of therapy. Also provided is a method of treatment, comprising administering to a subject in need of treatment a therapeutically-effective amount of an antibody or conjugate compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

Antibodies and conjugates of the disclosure may be administered alone or in combination with other treatments, either simultaneously or sequentially dependent upon the condition to be treated. Examples of treatments and therapies include, but are not limited to, chemotherapy (the administration of active agents, including, e.g. drugs, such as chemotherapeutics); surgery; and radiation therapy.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine;

pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), ofatumumab (ARZERRA®, GSK), pertuzumab (PERJETA™, OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Pharmaceutical compositions according to the present disclosure, and for use in accordance with the present disclosure, may comprise, in addition to the active ingredient, i.e. an antibody or conjugate compound of the disclosure, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

Use

The antibodies of the disclosure may be used to target a target location. The target location may preferably be a proliferative cell population.

The antibodies of the disclosure are antibodies for an antigen present on a proliferative cell population. In some embodiments the antigen is absent or present at a reduced level in a non proliferative cell population compared to the amount of antigen present in the proliferative cell population, for example a tumour cell population.

The target location may be in vitro, in vivo or ex vivo.

The antibodies of the disclosure include those with utility for anticancer activity. Thus, the present disclosure provides a humanised antibody as described herein for use in therapy. The present disclosure also provides a humanised antibody as described herein for use in the treatment of a proliferative disease. Similarly, the present disclosure provides the use of a humanised antibody as described herein in the manufacture of a medicament for treating a proliferative disease.

Also provided by the disclosure are antibody drug conjugates comprising a humanised antibody as described herein conjugated to a drug moiety. Such conjugates include those with utility for anticancer activity. In particular, the conjugates of the disclosure include an antibody conjugated, i.e. covalently attached by a linker, to a drug moiety, which may be a toxin. When the drug is not conjugated to an antibody, the drug has a cytotoxic effect. The biological activity of the drug moiety is thus modulated by conjugation to an antibody. The antibody-drug conjugates (ADC) of the disclosure may selectively deliver an effective dose of a cytotoxic agent to tumor tissue whereby greater selectivity, i.e. a lower efficacious dose, may be achieved.

Thus, the present disclosure provides a conjugate compound as described herein for use in therapy. The present disclosure also provides a conjugate compound as described herein for use in the treatment of a proliferative disease, and the use of a conjugate compound as described herein in the manufacture of a medicament for treating a proliferative disease.

One of ordinary skill in the art is readily able to determine whether or not a candidate conjugate treats a proliferative condition for any particular cell type.

The term "proliferative disease" pertains to an unwanted or uncontrolled cellular proliferation of excessive or abnormal cells which is undesired, such as, neoplastic or hyperplastic growth, whether in vitro or in vivo. Examples of proliferative conditions include, but are not limited to, benign, pre malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), lymphomas, leukemias, psoriasis, bone diseases, fibroproliferative disorders (e.g. of connective tissues), and atherosclerosis.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Disorders of particular interest include, but are not limited to cancers, including metastatic cancers and metastatic cancer cells, such as circulating tumour cells, which may be found circulating in body fluids such as blood or lymph. Cancers of particular interest include lung cancer, breast cancer, pancreatic cancer, ovarian cancer, renal cancer, head and neck cancer, mesothelioma, glioblastoma, melanomas, and brain tumors such as but not limited to gliomas, medulloblastoma, astrocytoma and ependymoma.

Other disorders of interest include any condition in which IL13Rα2 is overexpressed, or wherein IL-13Rα2 antagonism will provide a clinical benefit—for example in inflammatory conditions such as but not limited to inflammatory bowel disease and fibrosis.

It is contemplated that the antibodies and antibody-drug conjugates (ADC) of the present invention may be used to treat various diseases or disorders, e.g. characterized by the overexpression of a tumor antigen. Exemplary conditions or hyperproliferative disorders include benign or malignant tumors; leukemia, haematological, and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the ADC compounds may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g. Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Formulations

While it is possible for the antibodies and conjugate compounds of the disclosure to be used (e.g., administered) alone, it is often preferable to present it as a composition or formulation.

In some embodiments, the composition is a pharmaceutical composition (e.g., formulation, preparation, medicament) comprising an antibody or conjugate compound as described herein, and a pharmaceutically acceptable carrier, diluent, or excipient.

In some embodiments the composition is a pharmaceutical composition comprising at least one antibody or conjugate compound as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In some embodiments, the composition may further comprise other active agents, for example, other therapeutic or prophylactic agents. Suitable carriers, diluents, excipients, etc. can be found in standard pharmaceutical texts. See, for example, Handbook of Pharmaceutical Additives, 2nd Edition (eds. M. Ash and I. Ash), 2001 (Synapse Information Resources, Inc., Endicott, New York, USA), Remington's Pharmaceutical Sciences, 20th edition, pub. Lippincott, Williams & Wilkins, 2000; and Handbook of Pharmaceutical Excipients, 2nd edition, 1994.

Also disclosed are methods of making a pharmaceutical composition comprising admixing at least one [11C]-radiolabelled conjugate or conjugate-like compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations of the disclosure may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the antibodies, conjugate compounds, and compositions of the disclosure can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the conjugate compound is administered to a human patient according to the following dosage regime: about 50 or about 75 mg, 3 or 4 times daily.

In one embodiment, the conjugate compound is administered to a human patient according to the following dosage regime: about 100 or about 125 mg, 2 times daily.

The dosage amounts described above may apply to the antibody, conjugate (including the drug moiety and the linker to the antibody) or to the effective amount of drug compound provided, for example the amount of compound that is releasable after cleavage of the linker.

For the prevention or treatment of disease, the appropriate dosage will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises a course of administering an initial loading dose of about 4 mg/kg, followed by additional doses every week, two weeks, or three weeks of an ADC. Other dosage regimens may be useful. The progress of this therapy is easily monitored by conventional techniques and assays.

Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

Embodiments

The present disclosure provides anti-IL13Rα2 antibodies. Specifically contemplated embodiments of the antibodies of the disclosure include:

An antibody that binds to Interleukin-13 receptor subunit alpha-2 (IL13Rα2), comprising a heavy chain comprising the complementarity determining regions (CDRs) shown in SEQ ID NO:13, SEQ ID NO: 14 and SEQ ID: NO 15; and/or a light chain comprising (i) the CDRs shown in SEQ ID NO:16, SEQ ID NO: 17 and SEQ ID: NO 18; and (ii) a serine residue at position 30 (numbering with reference to SEQ ID NO: 3), wherein the variable regions are fully human. In one embodiment the antibody is fully human, including the constant regions. In a related embodiment the present invention provides an antibody conjugate comprising said antibody and pyrollobenzodiazepine dimer. In one embodiment the light chain is a human kappa light chain.

An antibody that binds to Interleukin-13 receptor subunit alpha-2 (IL13Rα2), wherein the antibody comprises a heavy chain variable region comprising an amino acid sequence selected from the group consisting of: SEQ ID NO: 3; SEQ ID NO: 5; SEQ ID NO: 6; SEQ ID NO: 7; and SEQ ID NO: 8. In some such embodiments, the antibody further comprises a light chain variable region which comprises a VL CDR1 with the amino acid sequence of SEQ ID NO: 16, a VL CDR2 with the amino acid sequence of SEQ ID NO: 17, and/or a VL CDR3 with the amino acid sequence of SEQ ID NO. 18. In some embodiments, the antibody further comprises a light chain variable region which comprises a VL CDR1 with the amino acid sequence of SEQ ID NO: 16, a VL CDR2 with the amino acid sequence of SEQ ID NO: 17, and a VL CDR3 with the amino acid sequence of SEQ ID NO. 18. In some embodiments the variable regions are fully human. In some embodiments the antibody is fully human. For example, any constant regions comprised in the antibody may also be fully human antibody.

Thus, in some embodiments, the antibody comprises:
(i) a heavy chain variable region having the amino acid sequence of: SEQ ID NO: 3, and a light chain variable region which comprises a VL CDR1 with the amino acid sequence of SEQ ID NO: 16, a VL CDR2 with the amino acid sequence of SEQ ID NO: 17, and a VL CDR3 with the amino acid sequence of SEQ ID NO. 18, optionally wherein the variable domains and/or the antibody is fully human;
(ii) a heavy chain variable region having the amino acid sequence of: SEQ ID NO: 5, and a light chain variable region which comprises a VL CDR1 with the amino acid sequence of SEQ ID NO: 16, a VL CDR2 with the amino acid sequence of SEQ ID NO: 17, and a VL CDR3 with the amino acid sequence of SEQ ID NO. 18, optionally wherein the variable domains and/or the antibody is fully human;
(iii) a heavy chain variable region having the amino acid sequence of: SEQ ID NO: 6, and a light chain variable region which comprises a VL CDR1 with the amino acid sequence of SEQ ID NO: 16, a VL CDR2 with the amino acid sequence of SEQ ID NO: 17, and a VL CDR3 with the amino acid sequence of SEQ ID NO. 18, optionally wherein the variable domains and/or the antibody is fully human;
(iv) a heavy chain variable region having the amino acid sequence of: SEQ ID NO: 7, and a light chain variable region which comprises a VL CDR1 with the amino acid sequence of SEQ ID NO: 16, a VL CDR2 with the amino acid sequence of SEQ ID NO: 17, and a VL CDR3 with the amino acid sequence of SEQ ID NO. 18, optionally wherein the variable domains and/or the antibody is fully human; or (v) a heavy chain variable region having the amino acid sequence of: SEQ ID NO: 8, and a light chain variable region which comprises a VL CDR1 with the amino acid sequence of SEQ ID NO: 16, a VL CDR2 with the amino acid sequence of SEQ ID NO: 17, and a VL CDR3 with the amino acid sequence of SEQ ID NO. 18, optionally wherein the variable domains and/or the antibody is fully human.

In some embodiments, the antibody further comprises a light chain variable region comprising an amino acid sequence selected from the group consisting of: SEQ ID NO: 4; SEQ ID NO: 9; SEQ ID NO: 10; SEQ ID NO: 11.

An antibody that binds to Interleukin-13 receptor subunit alpha-2 (IL13Rα2), wherein the antibody comprises a light chain variable region comprising an amino acid sequence selected from the group consisting of: SEQ ID NO: 4; SEQ ID NO: 9; SEQ ID NO: 10; SEQ ID NO: 11. In some such embodiments, the antibody further comprises a heavy chain variable region which comprises a VH CDR1 with the amino acid sequence of SEQ ID NO: 13, a VH CDR2 with the amino acid sequence of SEQ ID NO: 14, and/or a VH CDR3 with the amino acid sequence of SEQ ID NO: 15. In some embodiments, the antibody further comprises a heavy chain variable region which comprises a VH CDR1 with the amino acid sequence of SEQ ID NO: 13, a VH CDR2 with the amino acid sequence of SEQ ID NO: 14, and a VH CDR3 with the amino acid sequence of SEQ ID NO: 15. In some embodiments the variable regions are fully human. In some embodiments the antibody is fully human. For example, any constant regions comprised in the antibody may also be fully human antibody.

Thus, in some embodiments, the antibody comprises:

(i) a heavy chain variable region which comprises a VH CDR1 with the amino acid sequence of SEQ ID NO: 13, a VH CDR2 with the amino acid sequence of SEQ ID NO: 14, and a VH CDR3 with the amino acid sequence of SEQ ID NO. 15, and a light chain variable region having the amino acid sequence of: SEQ ID NO: 4, optionally wherein the variable domains and/or the antibody is fully human;

(ii) a heavy chain variable region which comprises a VH CDR1 with the amino acid sequence of SEQ ID NO: 13, a VH CDR2 with the amino acid sequence of SEQ ID NO: 14, and a VH CDR3 with the amino acid sequence of SEQ ID NO. 15, and a light chain variable region having the amino acid sequence of: SEQ ID NO: 9, optionally wherein the variable domains and/or the antibody is fully human;

(iii) a heavy chain variable region which comprises a VH CDR1 with the amino acid sequence of SEQ ID NO: 13, a VH CDR2 with the amino acid sequence of SEQ ID NO: 14, and a VH CDR3 with the amino acid sequence of SEQ ID NO. 15, and a light chain variable region having the amino acid sequence of: SEQ ID NO: 10, optionally wherein the variable domains and/or the antibody is fully human;

(iv) a heavy chain variable region which comprises a VH CDR1 with the amino acid sequence of SEQ ID NO: 13, a VH CDR2 with the amino acid sequence of SEQ ID NO: 14, and a VH CDR3 with the amino acid sequence of SEQ ID NO. 15, and a light chain variable region having the amino acid sequence of: SEQ ID NO: 11, optionally wherein the variable domains and/or the antibody is fully human.

In some embodiments, the antibody further comprises a heavy chain variable region comprising an amino acid sequence selected from the group consisting of: SEQ ID NO: 3; SEQ ID NO: 5; SEQ ID NO: 6; SEQ ID NO: 7; and SEQ ID NO: 8.

Thus, specifically contemplated antibodies of the disclosure include those which comprise:

i) a heavy chain variable region having the amino acid sequence of SEQ ID NO: 3, and a light chain variable region having the amino acid sequence of SEQ ID NO: 4;

ii) a heavy chain variable region having the amino acid sequence of SEQ ID NO: 3, and a light chain variable region having the amino acid sequence of SEQ ID NO: 9;

iii) a heavy chain variable region having the amino acid sequence of SEQ ID NO: 3, and a light chain variable region having the amino acid sequence of SEQ ID NO: 10;

iv) a heavy chain variable region having the amino acid sequence of SEQ ID NO: 3, and a light chain variable region having the amino acid sequence of SEQ ID NO: 11;

v) a heavy chain variable region having the amino acid sequence of SEQ ID NO: 5, and a light chain variable region having the amino acid sequence of SEQ ID NO: 4;

vi) a heavy chain variable region having the amino acid sequence of SEQ ID NO: 5, and a light chain variable region having the amino acid sequence of SEQ ID NO: 9;

vii) a heavy chain variable region having the amino acid sequence of SEQ ID NO: 5, and a light chain variable region having the amino acid sequence of SEQ ID NO: 10;

viii) a heavy chain variable region having the amino acid sequence of SEQ ID NO: 5, and a light chain variable region having the amino acid sequence of SEQ ID NO: 11;

ix) a heavy chain variable region having the amino acid sequence of SEQ ID NO: 6, and a light chain variable region having the amino acid sequence of SEQ ID NO: 4;

x) a heavy chain variable region having the amino acid sequence of SEQ ID NO: 6, and a light chain variable region having the amino acid sequence of SEQ ID NO: 9;

xi) a heavy chain variable region having the amino acid sequence of SEQ ID NO: 6, and a light chain variable region having the amino acid sequence of SEQ ID NO: 10;

xii) a heavy chain variable region having the amino acid sequence of SEQ ID NO: 6, and a light chain variable region having the amino acid sequence of SEQ ID NO: 11;

xiii) a heavy chain variable region having the amino acid sequence of SEQ ID NO: 7, and a light chain variable region having the amino acid sequence of SEQ ID NO: 4;

xiv) a heavy chain variable region having the amino acid sequence of SEQ ID NO: 7, and a light chain variable region having the amino acid sequence of SEQ ID NO: 9;

xv) a heavy chain variable region having the amino acid sequence of SEQ ID NO: 7, and a light chain variable region having the amino acid sequence of SEQ ID NO: 10;

xvi) a heavy chain variable region having the amino acid sequence of SEQ ID NO: 7, and a light chain variable region having the amino acid sequence of SEQ ID NO: 11;

xvii) a heavy chain variable region having the amino acid sequence of SEQ ID NO: 8, and a light chain variable region having the amino acid sequence of SEQ ID NO: 4;

xviii) a heavy chain variable region having the amino acid sequence of SEQ ID NO: 8, and a light chain variable region having the amino acid sequence of SEQ ID NO: 9;

xix) a heavy chain variable region having the amino acid sequence of SEQ ID NO: 8, and a light chain variable region having the amino acid sequence of SEQ ID NO: 10; and xx) a heavy chain variable region having the amino acid sequence of SEQ ID NO: 8, and a light chain variable region having the amino acid sequence of SEQ ID NO: 11.

Preferred antibodies of the disclosure include those which comprise:

a heavy chain variable region having the amino acid sequence of SEQ ID NO: 3 (VHA; HuCL47 VH), and a light chain variable region having the amino acid sequence of SEQ ID NO: 4 (VKA; HuCL47 VL);

a heavy chain variable region having the amino acid sequence of SEQ ID NO: 5 (VHAback), and a light chain variable region having the amino acid sequence of SEQ ID NO: 4 (VKA; HuCL47 VL); and a heavy chain variable region having the amino acid sequence of SEQ ID NO: 8 (VHA3), and a light chain variable region having the amino acid sequence of SEQ ID NO: 11 (VKA2).

Particularly preferred antibodies of the disclosure include those which comprise a heavy chain variable region having the amino acid sequence of: SEQ ID NO: 3, and a light chain variable region having the amino acid sequence of SEQ ID NO: 4.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

SEQUENCES

SEQ ID NO: 1 [murine CL47 VH, CDR underline]
QVQLQQPGAELVRPGASVKLSCKASGYTFSNYLMNWVKQRPEQDLDWIGRI
DPYDGDIDYNQNFKDKAILTVDKSSSTAYMQLSSLTSEDSAVYYCARGYGT
AYGVDYWGQGTSVTVSS SEQ ID NO: 2 [murine CL47 VL, CDR underline]
DIVLTQSPASLAVSLGQRATISCRASESVDNYGISFMNWFQQKPGQPPKLL
IYAASRQGSGVPARFSGSGSGTDFSLNIHPMEEDDTAMYFCQQSKEVPWTF
GGGTKLEIK SEQ ID NO: 3 [HuCL47 VH (Clone 47 VHA), CDR underline]
QVQLVQSGAEVKKPGASVKVSCKASGYTFSNYLMNWVRQAPGQGLEWMGRI
DPYDGDIDYNQNFKDRVTITRDTSASTAYMELSSLRSEDTAVYYCARGYGT
AYGVDYWGQGTSVTVSS SEQ ID NO: 4 [HuCL47 VL (Clone 47 VKA), CDR underline]
EIVLIQSPATLSLSPGERATLSCRASESVDNYGISFMNWYQQKPGQAPRLL
IYAASRQGSGIPDRFSGSGSGTDFTLTISRLEPEDFAVYYCQQSKEVPWTF
GGGTKLEIK SEQ ID NO: 5 [Clone 47 VHAback, CDR underline]
QVQLVQSGAEVKKPGASVKVSCKASGYTFSNYLMNWVRQAPGQGLEWIGRI
DPYDGDIDYNQNFKDRATLTVDKSASTAYMELSSLRSEDTAVYYCARGYGT
AYGVDYWGQGTSVTVSS SEQ ID NO: 6 [Clone 47 VHA1, CDR underline]
QVQLVQSGAEVKKPGASVKVSCKASGYTFSNYLMNWVRQAPGQGLEWIGRI
DPYDGDIDYNQNFKDRVTITRDTSASTAYMELSSLRSEDTAVYYCARGYGT
AYGVDYWGQGTSVTVSS SEQ ID NO: 7 [Clone 47 VHA2, CDR underline]
QVQLVQSGAEVKKPGASVKVSCKASGYTFSNYLMNWVRQAPGQGLEWMGRI
DPYDGDIDYNQNFKDRVTITVDTSASTAYMELSSLRSEDTAVYYCARGYGT
AYGVDYWGQGTSVTVSS SEQ ID NO: 8 [Clone 47 VHA3, CDR underline]
QVQLVQSGAEVKKPGASVKVSCKASGYTFSNYLMNWVRQAPGQGLEWMGRI
DPYDGDIDYNQNFKDRVTITRDKSASTAYMELSSLRSEDTAVYYCARGYGT
AYGVDYWGQGTSVTVSS SEQ ID NO: 9 [Clone 47 VKAback, CDR underline]
EIVLTQSPATLSLSPGERATLSCRASESVDNYGISFMNWFQQKPGQAPRLL
IYAASRQGSGIPDRFSGSGSGTDFTLTISRLEPEDFAVYFCQQSKEVPWTF
GGGTKLEIK SEQ ID NO: 10 [Clone 47 VKA1, CDR underline]
EIVLTQSPATLSLSPGERATLSCRASESVDNYGISFMNWFQQKPGQAPRLL
IYAASRQGSGIPDRFSGSGSGTDFTLTISRLEPEDFAVYYCQQSKEVPWTF
GGGTKLEIK SEQ ID NO: 11 [Clone 47 VKA2, CDR underline]
EIVLTQSPATLSLSPGERATLSCRASESVDNYGISFMNWYQQKPGQAPRLL
IYAASRQGSGIPDRFSGSGSGTDFTLTISRLEPEDFAVYFCQQSKEVPWTF
GGGTKLEIK -continued

SEQUENCES

SEQ ID NO: 12 [Extracellular domain (27-343) of
Human IL13RA2 (Uniprot Q14627)]
DTEIKVNPPQDFEIVDPGYLGYLYLQWQPPLSLDHFKECTVEYELKYRNIG
SETWKTIITKNLHYKDGFDLNKGIEAKIHILLPWQCTNGSEVQSSWAETTY
WISPQGIPETKVQDMDCVYYNWQYLLCSWKPGIGVLLDTNYNLFYWYEGLD
HALQCVDYIKADGQNIGCRFPYLEASDYKDFYICVNGSSENKPIRSSYFTF
QLQNIVKPLPPVYLTFTRESSCEIKLKWSIPLGPIPARCFDYEIEIREDDT
TLVTATVENETYTLKTTNETRQLCFVVRSKVNIYCSDDGIWSEWSDKQCWE
GEDLSKKILLRhhhhhh
Hhhhhh = C-terminal His Tag SEQ ID NO: 13 [HuCL47 CDRH1]
NYLMN SEQ ID NO: 14 [HuCL47 CDRH2]
RIDPYDGDIDYNQNFKD SEQ ID NO: 15 [HuCL47 CDRH3]
GYGTAYGVDY SEQ ID NO: 16 [HuCL47 CDRL1]
RASESVDNYGISFMN SEQ ID NO: 17 [HuCL47 CDRL2]
AASRQGS SEQ ID NO: 18 [HuCL47 CDRL3]
QQSKEVPWT

STATEMENTS OF DISCLOSURE

The following numbered statements, outlining aspects of the present disclosure, are part of the description.

101. An antibody that binds to Interleukin-13 receptor subunit alpha-2 (IL13Rα2), wherein the antibody comprises:
a heavy chain variable region comprising an amino acid sequence selected from the group consisting of: SEQ ID NO: 3; SEQ ID NO: 5; SEQ ID NO: 6; SEQ ID NO: 7; and SEQ ID NO: 8; and
a light chain variable region comprising an amino acid sequence selected from the group consisting of: SEQ ID NO: 4; SEQ ID NO: 9; SEQ ID NO: 10; SEQ ID NO: 11.

102. The antibody according to statement 101, wherein the antibody comprises a heavy chain variable region having the amino acid sequence of: SEQ ID NO: 3, and:
(i) a light chain variable region having the amino acid sequence of SEQ ID NO: 4;
(ii) a light chain variable region having the amino acid sequence of SEQ ID NO: 9;
(iii) a light chain variable region having the amino acid sequence of SEQ ID NO: 10; or
(iv) a light chain variable region having the amino acid sequence SEQ ID NO: 11.

103. The antibody according to statement 101, wherein the antibody comprises a heavy chain variable region having the amino acid sequence of: SEQ ID NO: 5, and:
(i) a light chain variable region having the amino acid sequence of SEQ ID NO: 4;
(ii) a light chain variable region having the amino acid sequence of SEQ ID NO: 9;
(iii) a light chain variable region having the amino acid sequence of SEQ ID NO: 10; or
(iv) a light chain variable region having the amino acid sequence SEQ ID NO: 11.

104. The antibody according to statement 101, wherein the antibody comprises a heavy chain variable region having the amino acid sequence of: SEQ ID NO: 6, and:
(i) a light chain variable region having the amino acid sequence of SEQ ID NO: 4;
(ii) a light chain variable region having the amino acid sequence of SEQ ID NO: 9;
(iii) a light chain variable region having the amino acid sequence of SEQ ID NO: 10; or
(iv) a light chain variable region having the amino acid sequence SEQ ID NO: 11.

105. The antibody according to statement 101, wherein the antibody comprises a heavy chain variable region having the amino acid sequence of: SEQ ID NO: 7, and:
(i) a light chain variable region having the amino acid sequence of SEQ ID NO: 4;
(ii) a light chain variable region having the amino acid sequence of SEQ ID NO: 9;
(iii) a light chain variable region having the amino acid sequence of SEQ ID NO: 10; or
(iv) a light chain variable region having the amino acid sequence SEQ ID NO: 11.

106. The antibody according to statement 101, wherein the antibody comprises a heavy chain variable region having the amino acid sequence of: SEQ ID NO: 8, and:
(i) a light chain variable region having the amino acid sequence of SEQ ID NO: 4;
(ii) a light chain variable region having the amino acid sequence of SEQ ID NO: 9;
(iii) a light chain variable region having the amino acid sequence of SEQ ID NO: 10; or
(iv) a light chain variable region having the amino acid sequence SEQ ID NO: 11.

107. The antibody according to statement 101 or 102, wherein the antibody comprises a heavy chain variable region having the amino acid sequence of: SEQ ID NO: 3, and a light chain variable region having the amino acid sequence of SEQ ID NO: 4.

108. The antibody according to any preceding statement, wherein the antibody is an antibody fragment selected from the group consisting of: a Fab, a Fab', a F(ab')2, and an scFv.

109. The antibody according to any preceding statement, wherein the antibody further comprises an antibody constant region derived from one or more human antibodies.

110. The antibody according to any preceding statement, wherein the antibody binds IL13Rα2 with an affinity ($K_D$) no greater than $5 \times 10^{-10}$ M, such as no greater than $2.5 \times 10^{-10}$ M.

111. The antibody according to any preceding statement, wherein the antibody binds IL13Rα2 with an affinity ($K_D$) no greater than $1.5 \times 10^{-10}$ M.

112. The antibody according to any preceding statement, wherein the antibody competitively inhibits the binding to IL13Rα2 of an antibody comprising a heavy chain variable region having the amino acid sequence of SEQ ID NO: 1 and a light chain variable region having the amino acid sequence of SEQ ID NO: 2, and optionally, an antibody constant region.

113. The antibody according to any preceding statement, wherein the antibody binds IL13Rα2 with higher affinity (KD) than an antibody comprising a heavy chain variable region having the amino acid sequence of SEQ ID NO: 1 and a light chain variable region having the amino acid sequence of SEQ ID NO: 2, and optionally, an antibody constant region.

114. The antibody according to any preceding statement, wherein the antibody has immunogenicity in a human subject that is lower than that of an antibody comprising a heavy chain variable region having the amino acid sequence of SEQ ID NO: 1 and a light chain variable region having the amino acid sequence of SEQ ID NO: 2, and optionally, an antibody constant region.

115. The antibody according to any preceding statement, wherein the antibody has improved stability properties as compared to an antibody comprising a heavy chain variable region having the amino acid sequence of SEQ ID NO: 1 and a light chain variable region having the amino acid sequence of SEQ ID NO: 2, and optionally, an antibody constant region.

116. An antibody drug conjugate comprising the antibody according to any preceding statement conjugated to a drug moiety.

117. The antibody drug conjugate according to statement 116, wherein the drug moiety is a cytotoxic drug moiety.

118. A pharmaceutical composition comprising the antibody or antibody drug conjugate according to any one of any one of statements 101 to 117 and a pharmaceutically acceptable diluent, carrier or excipient.

119. An antibody that binds to Interleukin-13 receptor subunit alpha-2 (IL13Rα2), wherein the antibody comprises:
 a heavy chain variable region comprising an amino acid sequence selected from the group consisting of: SEQ ID NO: 3; SEQ ID NO: 5; SEQ ID NO: 6; SEQ ID NO: 7; and SEQ ID NO: 8; and
 a light chain variable region which comprises a VL CDR1 with the amino acid sequence of SEQ ID NO: 16, a VL CDR2 with the amino acid sequence of SEQ ID NO: 17, and/or a VL CDR3 with the amino acid sequence of SEQ ID NO. 18.

120. The antibody according to statement 119, wherein the antibody comprises a light chain variable region which comprises a VL CDR1 with the amino acid sequence of SEQ ID NO: 16, a VL CDR2 with the amino acid sequence of SEQ ID NO: 17, and a VL CDR3 with the amino acid sequence of SEQ ID NO. 18.

121. The antibody according to statement 119 or 120, wherein the antibody comprises:
 (i) a heavy chain variable region having the amino acid sequence of: SEQ ID NO: 3, and a light chain variable region which comprises a VL CDR1 with the amino acid sequence of SEQ ID NO: 16, a VL CDR2 with the amino acid sequence of SEQ ID NO: 17, and a VL CDR3 with the amino acid sequence of SEQ ID NO. 18;
 (ii) a heavy chain variable region having the amino acid sequence of: SEQ ID NO: 5, and a light chain variable region which comprises a VL CDR1 with the amino acid sequence of SEQ ID NO: 16, a VL CDR2 with the amino acid sequence of SEQ ID NO: 17, and a VL CDR3 with the amino acid sequence of SEQ ID NO. 18;
 (iii) a heavy chain variable region having the amino acid sequence of: SEQ ID NO: 6, and a light chain variable region which comprises a VL CDR1 with the amino acid sequence of SEQ ID NO: 16, a VL CDR2 with the amino acid sequence of SEQ ID NO: 17, and a VL CDR3 with the amino acid sequence of SEQ ID NO. 18;
 (iv) a heavy chain variable region having the amino acid sequence of: SEQ ID NO: 7, and a light chain variable region which comprises a VL CDR1 with the amino acid sequence of SEQ ID NO: 16, a VL CDR2 with the amino acid sequence of SEQ ID NO: 17, and a VL CDR3 with the amino acid sequence of SEQ ID NO. 18; or
 (v) a heavy chain variable region having the amino acid sequence of: SEQ ID NO: 8, and a light chain variable region which comprises a VL CDR1 with the amino acid sequence of SEQ ID NO: 16, a VL CDR2 with the amino acid sequence of SEQ ID NO: 17, and a VL CDR3 with the amino acid sequence of SEQ ID NO. 18.

122. The antibody according to any one of statements 119-121, wherein the antibody comprises a light chain variable region comprising an amino acid sequence selected from the group consisting of: SEQ ID NO: 4; SEQ ID NO: 9; SEQ ID NO: 10; SEQ ID NO: 11.

123. An antibody that binds to Interleukin-13 receptor subunit alpha-2 (IL13Rα2), wherein the antibody comprises:
 a light chain variable region comprising an amino acid sequence selected from the group consisting of: SEQ ID NO: 4; SEQ ID NO: 9; SEQ ID NO: 10; SEQ ID NO: 11; and
 a heavy chain variable region which comprises a VH CDR1 with the amino acid sequence of SEQ ID NO: 13, a VH CDR2 with the amino acid sequence of SEQ ID NO: 14, and/or a VH CDR3 with the amino acid sequence of SEQ ID NO. 15.

124. The antibody according to statement 123, wherein the antibody comprises a VH CDR1 with the amino acid sequence of SEQ ID NO: 13, a VH CDR2 with the amino acid sequence of SEQ ID NO: 14, and a VH CDR3 with the amino acid sequence of SEQ ID NO. 15

125. The antibody according to statement 123 or 124, wherein the antibody comprises:
 (i) a heavy chain variable region which comprises a VH CDR1 with the amino acid sequence of SEQ ID NO: 13, a VH CDR2 with the amino acid sequence of SEQ ID NO: 14, and a VH CDR3 with the amino acid sequence of SEQ ID NO. 15, and a light chain variable region having the amino acid sequence of: SEQ ID NO: 4;
 (ii) a heavy chain variable region which comprises a VH CDR1 with the amino acid sequence of SEQ ID NO: 13, a VH CDR2 with the amino acid sequence of SEQ ID NO: 14, and a VH CDR3 with the amino acid sequence of SEQ ID NO. 15, and a light chain variable region having the amino acid sequence of: SEQ ID NO: 9;
 (iii) a heavy chain variable region which comprises a VH CDR1 with the amino acid sequence of SEQ ID NO: 13, a VH CDR2 with the amino acid sequence of SEQ ID NO: 14, and a VH CDR3 with the amino acid sequence of SEQ ID NO. 15, and a light chain variable region having the amino acid sequence of: SEQ ID NO: 10;
 (iv) a heavy chain variable region which comprises a VH CDR1 with the amino acid sequence of SEQ ID NO: 13, a VH CDR2 with the amino acid sequence of SEQ ID NO: 14, and a VH CDR3 with the amino acid sequence of SEQ ID NO. 15, and a light chain variable region having the amino acid sequence of: SEQ ID NO: 11.

126. The antibody according to any one of statements 123-125, wherein the antibody comprises a a heavy chain variable region comprising an amino acid sequence selected from the group consisting of: SEQ ID NO: 3; SEQ ID NO: 5; SEQ ID NO: 6; SEQ ID NO: 7; and SEQ ID NO: 8.

127. The antibody according to any one of statements 119-126, wherein the antibody comprises:
  i) a heavy chain variable region having the amino acid sequence of SEQ ID NO: 3, and a light chain variable region having the amino acid sequence of SEQ ID NO: 4;
  ii) a heavy chain variable region having the amino acid sequence of SEQ ID NO: 3, and a light chain variable region having the amino acid sequence of SEQ ID NO: 9;
  iii) a heavy chain variable region having the amino acid sequence of SEQ ID NO: 3, and a light chain variable region having the amino acid sequence of SEQ ID NO: 10;
  iv) a heavy chain variable region having the amino acid sequence of SEQ ID NO: 3, and a light chain variable region having the amino acid sequence of SEQ ID NO: 11;
  v) a heavy chain variable region having the amino acid sequence of SEQ ID NO: 5, and a light chain variable region having the amino acid sequence of SEQ ID NO: 4;
  vi) a heavy chain variable region having the amino acid sequence of SEQ ID NO: 5, and a light chain variable region having the amino acid sequence of SEQ ID NO: 9;
  vii) a heavy chain variable region having the amino acid sequence of SEQ ID NO: 5, and a light chain variable region having the amino acid sequence of SEQ ID NO: 10;
  viii) a heavy chain variable region having the amino acid sequence of SEQ ID NO: 5, and a light chain variable region having the amino acid sequence of SEQ ID NO: 11;
  ix) a heavy chain variable region having the amino acid sequence of SEQ ID NO: 6, and a light chain variable region having the amino acid sequence of SEQ ID NO: 4;
  x) a heavy chain variable region having the amino acid sequence of SEQ ID NO: 6, and a light chain variable region having the amino acid sequence of SEQ ID NO: 9;
  xi) a heavy chain variable region having the amino acid sequence of SEQ ID NO: 6, and a light chain variable region having the amino acid sequence of SEQ ID NO: 10;
  xii) a heavy chain variable region having the amino acid sequence of SEQ ID NO: 6, and a light chain variable region having the amino acid sequence of SEQ ID NO: 11;
  xiii) a heavy chain variable region having the amino acid sequence of SEQ ID NO: 7, and a light chain variable region having the amino acid sequence of SEQ ID NO: 4;
  xiv) a heavy chain variable region having the amino acid sequence of SEQ ID NO: 7, and a light chain variable region having the amino acid sequence of SEQ ID NO: 9;
  xv) a heavy chain variable region having the amino acid sequence of SEQ ID NO: 7, and a light chain variable region having the amino acid sequence of SEQ ID NO: 10;
  xvi) a heavy chain variable region having the amino acid sequence of SEQ ID NO: 7, and a light chain variable region having the amino acid sequence of SEQ ID NO: 11;
  xvii) a heavy chain variable region having the amino acid sequence of SEQ ID NO: 8, and a light chain variable region having the amino acid sequence of SEQ ID NO: 4;
  xviii) a heavy chain variable region having the amino acid sequence of SEQ ID NO: 8, and a light chain variable region having the amino acid sequence of SEQ ID NO: 9;
  xix) a heavy chain variable region having the amino acid sequence of SEQ ID NO: 8, and a light chain variable region having the amino acid sequence of SEQ ID NO: 10; or
  xx) a heavy chain variable region having the amino acid sequence of SEQ ID NO: 8, and a light chain variable region having the amino acid sequence of SEQ ID NO: 11.

128. The antibody according to any one of statements 119-127, wherein the antibody comprises a heavy chain variable region having the amino acid sequence of: SEQ ID NO: 3, and a light chain variable region having the amino acid sequence of SEQ ID NO: 4.

129. An antibody comprising:
  a heavy chain variable region which comprises a VH CDR1 with the amino acid sequence of SEQ ID NO: 13, a VH CDR2 with the amino acid sequence of SEQ ID NO: 14, and/or a VH CDR3 with the amino acid sequence of SEQ ID NO: 15; and/or
  a light chain variable region which comprises a VL CDR1 with the amino acid sequence of SEQ ID NO: 16, a VL CDR2 with the amino acid sequence of SEQ ID NO: 17, and/or a VL CDR3 with the amino acid sequence of SEQ ID NO. 18.

130. The antibody according to statement 129, wherein the antibody binds to Interleukin-13 receptor subunit alpha-2 (IL13Rα2).

131. The antibody according to either one of statements 129 or 130, wherein the antibody comprises a serine residue at position 30 (numbering with reference to SEQ ID NO: 3).

132. The antibody according to any one of statements any one of statements 129 to 131, wherein the variable regions are fully human.

133. The antibody according to any one of statements any one of statements 129 to 132, wherein the antibody is a fully human antibody.

134. The antibody according to any one of statements any one of statements 129 to 133, wherein the light chain is a human kappa light chain.

135. The antibody according to any one of statements 119-134, wherein the antibody is an antibody fragment selected from the group consisting of: a Fab, a Fab', a F(ab')2, and an scFv.

136. The antibody according to any one of statements 119-134, wherein the antibody further comprises an antibody constant region derived from one or more human antibodies.

137. The antibody according to any one of statements 119-136, wherein the antibody binds IL13Rα2 with an affinity ($K_D$) no greater than $5\times10^{-10}$ M, such as no greater than $2.5\times10^{-10}$ M.

138. The antibody according to any one of statements 119-137, wherein the antibody binds IL13Rα2 with an affinity ($K_D$) no greater than $1.5\times10^{-10}$ M.

139. The antibody according to any one of statements 119-138, wherein the antibody competitively inhibits the binding to IL13Rα2 of an antibody comprising a heavy chain variable region having the amino acid sequence of SEQ ID NO: 1 and a light chain variable region having the amino acid sequence of SEQ ID NO: 2, and optionally, an antibody constant region.

140. The antibody according to any one of statements 119-139, wherein the antibody binds IL13Rα2 with higher affinity (KD) than an antibody comprising a heavy chain variable region having the amino acid sequence of SEQ ID NO: 1 and a light chain variable region having the amino acid sequence of SEQ ID NO: 2, and optionally, an antibody constant region.

141. The antibody according to any one of statements 119-140, wherein the antibody has immunogenicity in a human subject that is lower than that of an antibody comprising a heavy chain variable region having the amino acid sequence of SEQ ID NO: 1 and a light chain variable region having the amino acid sequence of SEQ ID NO: 2, and optionally, an antibody constant region.

142. The antibody according to any any one of statements 119-141, wherein the antibody has improved stability properties as compared to an antibody comprising a heavy chain variable region having the amino acid sequence of SEQ ID NO: 1 and a light chain variable region having the amino acid sequence of SEQ ID NO: 2, and optionally, an antibody constant region.

143. An antibody drug conjugate comprising the antibody according to any one of statements 119-142 conjugated to a drug moiety.

144. The antibody drug conjugate according to statement 143, wherein the drug moiety is a cytotoxic drug moiety.

145. The antibody drug conjugate according to statement 144, wherein the cytotoxic drug moiety is a pyrollobenzodiazepine dimer.

146. A pharmaceutical composition comprising the antibody or antibody drug conjugate according to any one of any one of statements 119 to 145 and a pharmaceutically acceptable diluent, carrier or excipient.

201. The antibody, antibody drug conjugate, or pharmaceutical composition according to any one of statements 101 to 146, for use in a method of treatment.

202. The antibody, antibody drug conjugate, or pharmaceutical composition according to any one of statements 101 to 146, for use in a method of treatment of a proliferative disease in a subject.

203. The antibody, antibody drug conjugate, or pharmaceutical composition according to statement 202, wherein the proliferative disease is cancer.

204. The antibody, antibody drug conjugate, or pharmaceutical composition according to statement 203, wherein the cancer is a cancer selected from the group consisting of: lung cancer, breast cancer, pancreatic cancer, ovarian cancer, renal cancer, head and neck cancer, mesothelioma, glioblastoma, melanomas, and brain tumors such as but not limited to gliomas, medulloblastoma, astrocytoma and ependymoma.

205. Use of an antibody, antibody drug conjugate, or pharmaceutical composition according to any one of statements 101 to 146, in the manufacture of a medicament for use in a method of treatment.

206. Use of an antibody, antibody drug conjugate, or pharmaceutical composition according to any one of statements 101 to 146, in the manufacture of a medicament for use in a method of treatment of a proliferative disease in a subject.

207. The use according to statement 206, wherein the proliferative disease is cancer.

208. The use according to statement 207, wherein the cancer is a cancer selected from the group consisting of: lung cancer, breast cancer, pancreatic cancer, ovarian cancer, renal cancer, head and neck cancer, mesothelioma, glioblastoma, melanomas, and brain tumors such as but not limited to gliomas, medulloblastoma, astrocytoma and ependymoma.

209. A method of treating a proliferative disease comprising administering to a subject in need thereof an antibody, antibody drug conjugate, or pharmaceutical composition according to any one of statements 101 to 146.

210. The method according to statement 209 wherein the subject is administered a chemotherapeutic agent in combination with the antibody, antibody drug conjugate, or pharmaceutical composition.

211. The method according to any one of statements 208 to 210, wherein the cancer is a cancer selected from the group consisting of: lung cancer, breast cancer, pancreatic cancer, ovarian cancer, renal cancer, head and neck cancer, mesothelioma, glioblastoma, melanomas, and brain tumors such as but not limited to gliomas, medulloblastoma, astrocytoma and ependymoma.

301. A polynucleotide encoding an antibody according to any one of statements 101 to 115 or 119 to 142.

302. A vector comprising the polynucleotide of statement 301.

303. The vector of statement 302 wherein the vector is an expression vector.

304. A host cell comprising a vector according to any one of statements 302 to 303.

305. The host cell according to statement 304, wherein the host cell is prokaryotic, eukaryotic, or mammalian.

EXAMPLES

Materials and Methods

Expression and Purification of Antibodies

Cell lines were cultured and expanded according to the manufacturer's instructions; Expi293F™ cells were grown in Expi293™ Expression Medium (ThermoFisher A1435102). Briefly, the cells were cultured in 125 mL shaker culture flasks (Corning™ 431143) in a 37° C. orbital incubator, at 125 rpm and 8% CO2 atmosphere, and maintained at $3\text{-}5\times10^6$ cells/ml throughout the method. Cell density was determined in duplicate by Trypan blue exclusion assay using a LUNA-II™ automated cell counter (Logo Biosystems Ltd). DNA transfection procedures in volumes of 30 mL were followed for both cell lines as described in Thermo Fisher protocols. On the day of transfection, cells with >95% viability (examined via a microscope/cell counter) were selected and diluted to $2.5\times10^6$/ml for Expi293F™ in 25.5 mL of cell specific expression medium. For Expi293F™ 30 µg of plasmid DNA (15 µg heavy chain+15 µg light chain) was diluted in Opti-MEM® I Reduced-Serum Medium (ThermoFisher 31985070) to a total of 1.5 mL, simultaneously in a separate vial 81 µL of Expi-Fectamine™293 Reagent was diluted in Opti-MEM® I Reduced Serum Medium to a total of 1.5 mL. Each was gently mixed and incubated at room temperature for 5 minutes, then combined carefully to obtain a total volume of 3 mL. This was incubated for a further 20 minutes at room temperature to allow the DNA-lipid complexes to form, following this the mixture was carefully added to the cell flask. Cultures were harvested on Day 5, cell viability and density were measured using a LUNA-II™ automated cell counter, as described earlier. To harvest, cells were centrifuged (2000 G, 15 min, 4° C.) and the supernatant was removed and then sterile filtered through 0.22 μm filters prior to purification. Purification was by standard Protein A chromatography.

ELISA

Recombinant human extracellular domain of IL13RA2-6His (27-343) was obtained from Sino Biological (Ref 10350-H08H). 50 μl of 1 μg/ml of human IL13RA2 in PBS was coated overnight at 4° C. on MaxiSorp ELISA plates. The following morning, the plate is washed with PBS/Tween20 0.02%. Each well has 200 μl of Superblock blocking buffer added and incubated at room temperature for 1 hour in an orbital shaker at 120 rpm. A dilution series of each antibody was prepared, with dilutions of each antibody variant in PBS/Tween20 0.02%. The antibodies are added to blocked antigen coated plates and incubated for 1 hour at room temperature with 120 rpm shaking on an orbital shaker. Plates are then washed 3-times with 200 μl of PBS/Tween20 0.02% and 75 μl of secondary antibody (Mouse anti-human-HRP diluted 1 in 4000 in PBS/Tween20 0.02%) is added to the wells and incubated for 1 hour at room temperature with 120 rpm shaking on an orbital shaker. Plates are then washed 3-times with 200 μl of PBS/Tween20 0.02%. To develop the ELISA, 75 μl of TMB-Turbo substrate is added to the wells and incubated at room temperature with 120 rpm shaking on an orbital shaker till a blue colour develops, the reaction is then stopped with the addition of 75 μl of 0.6 N HCl. Plates are read on the Envision at 450 nM and curves are analysed using GraphPad prism software Thermal Shift Analysis Protein thermal shift dye, 2.5 μL 1:1000 dilution ((Life Technologies cat. 446148) was added to sample proteins (17.5 μL of 0.5 mg/mL in PBS) in a 96 well optical plate and mixed thoroughly. Every sample was done in quadruplicate. The plate was sealed with an optical adhesive film and bubbles in the wells were removed by centrifugation 1 min at 500 g, then placed on ice. The sealed plate was introduced in the 7500 Real-Time PCR System and subsequently the experiment was set up as follows:

| | Reaction vol 20 μl | | |
| | Ramp mode continuous | | |
| Step | Ramp rate | Temp ° C. | Time (mm:ss) |
| --- | --- | --- | --- |
| 1 | 100% | 25.0 | 02:00 |
| 2 | 1% | 99.0 | 02:00 |

The data was analysed using the Protein thermal shift v1.2 software (Life Technologies).

Accelerated Stability Analysis

Antibodies were incubated at 45° C. in sterile PBS for 7-8 days before being analysed by ELISA, SEC, HIC and RP Chromatography.

Biacore Analysis

Biacore analysis using Human IL13RA2-6His coated sensor was used to calculate apparent affinity constants of the Clone 47 variants. A dilution series of the antibody variants were applied to the IL13RA2 sensor surface for 600 seconds minutes to calculate the association constant Ka and buffer (HBS-EP+) was then applied for 1800 seconds to calculate the dissociation constant Kd. The ratio of the two constants will provide an apparent KD as the bivalency of the antibody will affect the binding kinetics.

HPLC Size Exclusion Chromatography (SEC)

SEC analysis was carried out using a Shimadzu HPLC system (or equivalent system), using TSKgel Super SW mAb HTP 4 um 4.6 mm×15 cm column. The mobile phase was 200 mM Potassium Phosphate, 250 mM Potassium Chloride, 10% v/v i-Propanol, pH 6.95, with a flowrate of 0.5 ml/minute and detection at 280 nm.

HPLC Hydrophobic Interaction Chromatography (HIC)

HIC analysis SEC analysis was carried out using a Shimadzu HPLC system (or equivalent system), using a Proteomix HIC Butyl-NP5, 5 um, non-porous, 4.6×35 mm (Sepax) column. Mobile Phase A was 1.25 M $(NH_4)_2SO_4$, 25 mM NaOAc (pH 5.50) and Mobile Phase B was 75% 25 mM NaOAc (pH 5.50), 25% i-Propanol, with a flowrate of 0.8 ml/minute and detection at 214 nm.

HPLC Reverse Phase Chromatography

Reverse Phase chromatography was carried out using Shimadzu HPLC system (or equivalent system), using a Aeris Widepore XB-C18, 200 Å, 3.6 μm, 2.1×150 mm (Phenomenex, 00F-4482-AN) column. Mobile Phase A was water+0.1% v/v TFA and Mobile Phase B was Acetonitrile+0.1% v/v TFA. The sample was prepared prior to loading by addition to 40 μL of sample (5 mg/ml) to which was added 30 μl of water, 20 μl NaBorate and 10 μL of DTT. This was then incubated at 37° C., 30 min, 100 μl of 49:49:2 Acetonitrile/Water/Formic acid was added. The column was run at 1 mL/minute, at a temperature of 80° C., with detection at 214 nm.

In Vitro Cytotoxicity

A375/NCl—H1299 cells were diluted to $5\times10^4$ cells/mL in complete growth with 100 μL of cells added to wells in an EDGE plate. The cells were incubated at 37° C./5% C02 for 2-6 hours to allow time for the cells to adhere. The ADC's were diluted in an 11 point, 1 in 4 serial dilutions, from 50 μg/mL to 47.7 μg/mL, leaving a final negative control sample i.e. no ADC, each concentration was run in duplicate. The diluted ADC's were added to the EDGE plate containing the target cells, and the plate was incubated in a humidified incubator for 5 days (~120 hours). To determine the cytotoxic effect of the ADC's, Cell Titre Glow (Promega) was used, 40 μL of the read solution was added to each well on the plate and incubated at 37° C./5% C02 for 1-5 hours. After the incubation, the plate was read on an optical reader (Molecular Devices Spectramax i3X) and the data analysed by the software inherent to the machine (Softmax Pro). Overall the data is a result of running each cell line in triplicate.

FACS Analysis

NCl—H1299 cells were diluted to $2\times10^6$ cells/mL in assay buffer (0.1% BSA/0.1% Sodium Azide in PBS) and 50 μL added per well to a 96-well-plate. The HuCL47 and Clone 47 antibodies were diluted to a top concentration of 40 μg/ml (266 nM) of and diluted 1:4 for 7 dilutions as well as buffer only. 50 μL of the antibody were added to 50 μL of cells to give a concentration of 20 μg/ml. The plate was incubated for 1 hour at room temperature, after which the plate was centrifuged and washed three times. A Goat F(ab')2 Anti-Human IgG Alexa Fluor 488-conjugated antibody was used (Life Technologies Cat. No. H10120) at a 1 in 250 dilution for detection in assay buffer, 50 μL added to cells and after one hour of incubation at room temperature the cells centrifuged and washed as before, fixed with 7.5% formaldehyde and analysed on the Flow cytometer, with data analysis carried out using FlowJo.

Example 1—Design and Production of Humanised Antibodies

A number of humanised anti-Interleukin-13 receptor subunit alpha-2 (IL13Rα2) antibody variants were generated beginning from the murine anti-IL13Rα2 antibody "Clone 47". The heavy and light chain variable region sequences of murine "Clone 47" are SEQ ID NO: 1 and SEQ ID NO: 2 respectively. These were compared with the human variable fragment database, and human framework regions with highest homology to Clone 47 at Vernier and canonical residues were selected for CDR grafting.

For VH humanisation, IGHV1-3 and IGHJ1-01 frameworks were selected for CDR grafting. The threonine T30 in the original IGHV1-3 human framework was replaced by a serine S30, which is also very common at this position in human germlines, and which matches the serine found in this position in the murine VH sequence. The resulting humanised VH domain (SEQ ID NO: 3) was designated "Clone 47 VHA".

Further humanised versions of the Clone 47 VH were generated by introducing back mutations into the "Clone 47 VHA" (SEQ ID NO: 3) sequence. These humanised VH domains were designated "Clone 47 VHAback" (SEQ ID NO: 5), "Clone 47 VHA1" (SEQ ID NO: 6), "Clone 47 VHA2" (SEQ ID NO: 7), and "Clone 47 VHA3" (SEQ ID NO: 8). The variants "Clone 47 VHA1", "Clone 47 VHA2", and "Clone 47 VHA3" were generated to assess the impact of murine VCl residues M48, V71, and K73 respectively (numbering according to Kabat).

For VL humanisation, IGKV3-NL5 and IGHJ2-01 frameworks were selected for CDR grafting. The resulting humanised VL domain (SEQ ID NO: 4) was designated "Clone 47 VKA".

Further humanised versions of the Clone 47 VL were generated by introducing back mutations into the "Clone 47 VKA" (SEQ ID NO: 4) sequence. These humanised VL domains were designated "Clone 47 VKAback" (SEQ ID NO: 9), "Clone 47 VKA1" (SEQ ID NO: 10), and "Clone 47 VKA2" (SEQ ID NO: 11). The variants "Clone 47 VKA1" and "Clone 47 VKA2" were generated to assess the impact of two murine VCl phenylalanine residues F36 and F87, which are both tyrosine residues in the human germline.

Each of the generated light and heavy chain variants were cloned and paired up, transfected into Expi293 cells, expressed and purified. Table 1 shows expression levels and antibody yields of transient co-transfection of the heavy and light chain constructs in Expi293 cells. 3 ml of purified antibodies was obtained. Clones marked with (*) had expression levels over 200 µg/ml and were selected for further analysis.

TABLE 1

Expression of humanised variants

| VH construct | VK construct | IgG µg/ml | Yield (mg) |
|---|---|---|---|
| Clone 47 VHA* | Clone 47 VKA | 281 | 0.843 |
| Clone 47 VHA | Clone 47 VKAback | 175 | 0.525 |

TABLE 1-continued

Expression of humanised variants

| VH construct | VK construct | IgG µg/ml | Yield (mg) |
|---|---|---|---|
| Clone 47 VHA* | Clone 47 VKA1 | 231 | 0.693 |
| Clone 47 VHA* | Clone 47 VKA2 | 300 | 0.900 |
| Clone 47 VHAback* | Clone 47 VKA | 312 | 0.936 |
| Clone 47 VHAback | Clone 47 VKAback | 100 | 0.300 |
| Clone 47 VHAback* | Clone 47 VKA1 | 243 | 0.729 |
| Clone 47 VHAback* | Clone 47 VKA2 | 212 | 0.636 |
| Clone 47 VHA1 | Clone 47 VKA | 175 | 0.525 |
| Clone 47 VHA1 | Clone 47 VKAback | 112 | 0.336 |
| Clone 47 VHA1 | Clone 47 VKA1 | 175 | 0.525 |
| Clone 47 VHA1 | Clone 47 VKA2 | 143 | 0.429 |
| Clone 47 VHA2 | Clone 47 VKA | 187 | 0.561 |
| Clone 47 VHA2 | Clone 47 VKAback | 131 | 0.393 |
| Clone 47 VHA2 | Clone 47 VKA1 | 187 | 0.561 |
| Clone 47 VHA2 | Clone 47 VKA2 | 168 | 0.504 |
| Clone 47 VHA3 | Clone 47 VKA | 156 | 0.468 |
| Clone 47 VHA3 | Clone 47 VKAback | 137 | 0.411 |
| Clone 47 VHA3 | Clone 47 VKA1 | 81 | 0.243 |
| Clone 47 VHA3* | Clone 47 VKA2 | 200 | 0.600 |

Binding of each humanised clone to IL13Rα2 was assessed by ELISA. All tested clones appear similar in their binding to IL13Rα2.

Example 2—Characterisation of the Humanised Antibodies

Binding affinity of a chimeric (Ch) Clone 47 and select humanised variants to human IL13Rα2 was measured on Biacore. Results are shown in Table 2 below. The apparent affinities show that the humanised variants show improved binding to human IL13Rα2 as compared to the chimeric (Ch) Clone 47.

TABLE 2

| Variants | $K_{ass}$ (1/MS) | $K_{diss}$ (1/s) | $K_{D\,App}$ (nM) |
|---|---|---|---|
| Ch Clone 47 | $1.25 \times 10^5$ | $6.58 \times 10^{-5}$ | 0.53 |
| VHA/VKA | $1.12 \times 10^5$ | $1.12 \times 10^{-5}$ | 0.10 |
| VHA/VKA1 | $1.24 \times 10^5$ | $2.65 \times 10^{-5}$ | 0.21 |
| VHA/VKA2 | $1.31 \times 10^5$ | $8.20 \times 10^{-6}$ | 0.06 |
| VHAback/VKA | $1.15 \times 10^5$ | $5.30 \times 10^{-6}$ | 0.05 |

Stability of a chimeric Clone 47 and select humanised variants was assessed by protein thermal shift and temperature stability assays at 37° C. versus 4° C. for 8 days. Results are shown in Table 3 below. The selected humanised variants subjected to stress conditions show comparable stability to the chimeric Clone 47.

TABLE 3

| | | 8 Days stability (PBS) | | | | | |
|---|---|---|---|---|---|---|---|
| | | 4° C. | | | 37° C. | | |
| Clones | PTS $T_m$ | SEC | RP | HIC | SEC | RP | HIC |
| Ch Clone 47 | 71.4 | 4.86/97.0 | 3.80/3.48 | 2.19 | 4.88/84.9 | 3.80/3.47 | 2.19 |
| VHA/VKA | 73.1 | 4.84/96.8 | 3.79/3.42 | 2.18 | 4.85/89.6 | 3.79/3.41 | 2.18 |
| VHA/VKA1 | 70.3 | 4.84/96.6 | 3.79/3.45 | 2.19 | 4.84/89.2 | 3.79/3.55 | 2.18 |
| VHA/VKA2 | 72.0 | 4.87/93.0 | 3.78/3.52 | 2.19 | 4.85/92.6 | 3.78/3.53 | 2.18 |
| VHAback/VKA | 74.1 | 4.82/97.3 | 3.78/3.40 | 2.19 | 4.83/93.1 | 3.78/3.39 | 2.18 |

TABLE 3-continued

| | | 8 Days stability (PBS) | | | | | |
| --- | --- | --- | --- | --- | --- | --- | --- |
| | | 4° C. | | | 37° C. | | |
| Clones | PTS T$_m$ | SEC | RP | HIC | SEC | RP | HIC |
| VHAback/VKA1 | 72.3 | 4.82/97.8 | 3.79/3.43 | 2.19 | 4.83/91.2 | 3.80/3.54 | 2.19 |
| VHA3/VKA2 | 71.9 | 4.83/97.5 | 3.76/3.42 | 2.19 | 4.84/92.1 | 3.75/3.52 | 2.19 |

Protein thermal shift (PTS): Mean Tm in ° C. (quadruplicates)
SEC: Elution time (min)/% Monomer
RP: HC/LC retention time (min)
HIC: Retention time (min)

Binding of the variants listed in Table 3 to IL13Rα2 was also assessed by ELISA following incubation at 4° C. or 45° C. for 8 days. As shown in Table 4, among the tested variants only the VHANKA variant showed no reduction in binding due to the stress conditions (incubation at 45° C. for 8 days), indicating it is the most stable. These binding data also indicate that the humanised variants VHAback/VKA and VHA3NKA2 have improved stability properties as compared to the chimeric Clone 47.

TABLE 4

| Clone 47 variants | EC$_{50}$ 45° C. (ng/ml) | EC$_{50}$ 4° C. (ng/ml) |
| --- | --- | --- |
| Ch Clone 47 | 16.8 | 77.7 |
| VHA/VKA | 18.4 | 17.8 |
| VHA/VKA1 | 12.3 | 58.1 |
| VHA/VKA2 | 20.4 | 147.9 |
| VHAback/VKA | 16.4 | 45.6 |
| VHAback/VKA1 | 12.8 | 1012.0 |
| VHA3/VKA2 | 12.3 | 25.8 |

Based on this data, the VHANKA variant (which is fully human with no mouse back mutations introduced) comprising the VH of SEQ ID NO: 3 and VL of SEQ ID NO: 4 is the best performing. This humanised anti-IL13Rα2 antibody was designated "HuCL47".

A sequence comparison of murine "Clone 47" and "HuCL47" is shown in FIG. 1.

Example 3—Theoretical pI of Anti-IL13Rα2 Antibodies

The theoretical pIs of certain of the anti-IL13Rα2 antibodies described above were calculated based on their heavy and light chain sequences using the "Protparam" tool available at web.expasy.org/protparam/. Results are shown in Table 5.

TABLE 5

| Antibody | VH/VL Sequences | pI |
| --- | --- | --- |
| Ch Clone 47 | SEQ ID NO: 1/SEQ ID NO: 2 | 6.95 |
| VHA/VKA (HuCL47) | SEQ ID NO: 3/SEQ ID NO: 4 | 7.63 |

TABLE 5-continued

| Antibody | VH/VL Sequences | pI |
| --- | --- | --- |
| VHAback/VKAback | SEQ ID NO: 5/SEQ ID NO: 9 | 7.64 |
| VHA1/VKA1 | SEQ ID NO: 6/SEQ ID NO: 10 | 7.64 |
| VHA2/VKA2 | SEQ ID NO: 7/SEQ ID NO: 11 | 7.28 |

Example 4—Comparison of Clone 47 and HuCL47

Chimeric clone 47 and HuCL47 were compared in terms of their: binding to NCl—H1299 Cells by standard FACS analysis using NCl—H1299 cells and unmodified purified antibodies. In vitro cytotoxicity analysis was performed on both A375 and NCl-1299 cells, using a pyrollobenzodiazepine dimer (PBD) warhead conjugated to chimeric clone 47 and HuCL47.

Figure 2:
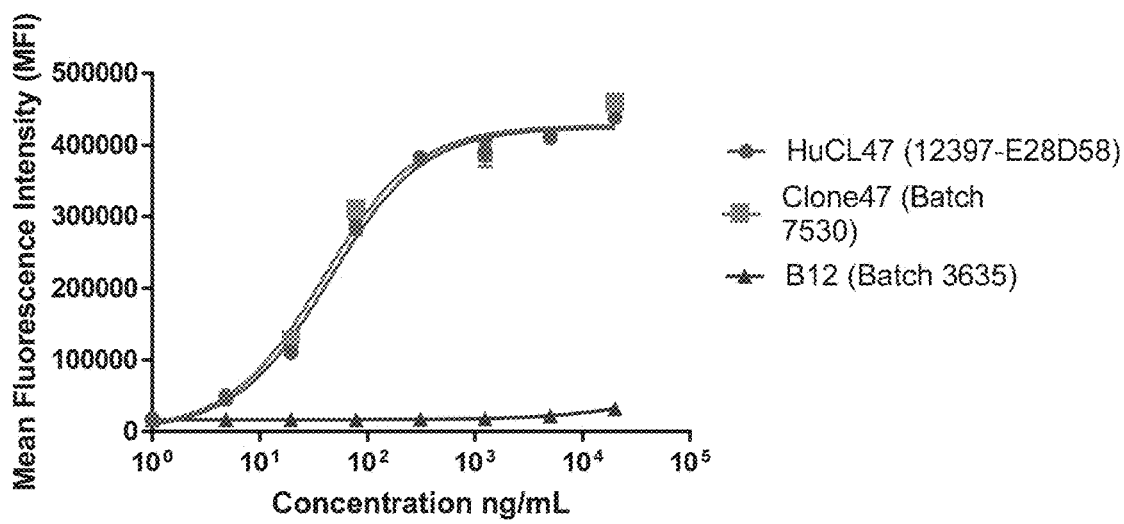
FIG. 2 Comparison of murine Clone47, humanised variant HuCL47, and isotype control B12 antibodies binding to NCl—H1299 Cells.
Figure 3:
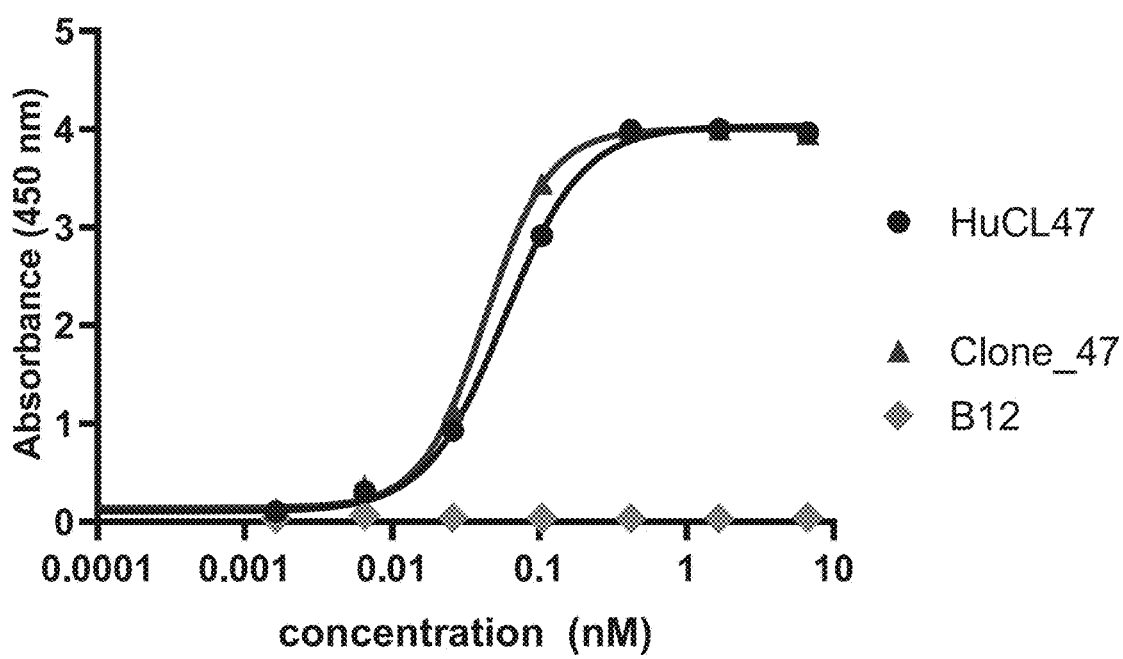
FIG. 3 ELISA binding comparison of murine Clone47, humanised variant HuCL47, and isotype control B12 antibodies.

Results are shown in: FIG. 2 (binding to NCl—H1299 Cells), FIG. 3 (binding to IL13Rα2), Table 6 (cytotoxicity to NCl—H1299 Cells), and Table 7 (cytotoxicity to A-375 Cells).

TABLE 6

| ADC | EC$_{50}$ (pM) |
| --- | --- |
| Ch Clone 47-PBD | 135.3 |
| VHA/VKA (HuCL47)-PBD | 113.7 |
| B12-PBD | 12400 |

TABLE 7

| ADC | EC$_{50}$ (pM) |
| --- | --- |
| Ch Clone 47-PBD | 7.6 |
| VHA/VKA (HuCL47)-PBD | 7.8 |
| B12-PBD | 6864 |

REFERENCES

A number of publications are cited above in order to more fully describe and disclose the invention and the state of the art to which the invention pertains The entirety of each of these references is incorporated herein.

For standard molecular biology techniques, see Sambrook, J., Russel, D. W. Molecular Cloning, A Laboratory Manual. 3 ed. 2001, Cold Spring Harbor, New York: Cold Spring Harbor Laboratory Press

The invention claimed is:

1. An antibody that binds to Interleukin-13 receptor subunit alpha-2 (IL13Rα2), which comprises a heavy chain variable region comprising the amino acid sequence of SEQ ID NO: 3 and a light chain variable region comprising the amino acid sequence of SEQ ID NO: 4.

2. The antibody according to claim 1, wherein the antibody binds IL13Rα2 with an affinity ($K_D$) no greater than $5 \times 10^{-10}$ M.

3. The antibody according to claim 1, wherein the antibody competitively inhibits the binding to IL13Rα2 of an antibody comprising a heavy chain variable region having the amino acid sequence of SEQ ID NO: 1 and a light chain variable region having the amino acid sequence of SEQ ID NO: 2.

4. The antibody according to claim 1, wherein the antibody binds IL13Rα2 with higher affinity ($K_D$) than an antibody comprising a heavy chain variable region having the amino acid sequence of SEQ ID NO: 1 and a light chain variable region having the amino acid sequence of SEQ ID NO: 2.

5. The antibody according to claim 1, wherein the antibody has immunogenicity in a human subject that is lower than that of an antibody comprising a heavy chain variable region having the amino acid sequence of SEQ ID NO: 1 and a light chain variable region having the amino acid sequence of SEQ ID NO: 2.

6. The antibody according to claim 1, wherein the antibody has improved stability properties as compared to an antibody comprising a heavy chain variable region having the amino acid sequence of SEQ ID NO: 1 and a light chain variable region having the amino acid sequence of SEQ ID NO: 2.

7. The antibody according to claim 1, wherein the antibody comprises a constant region of isotype IgG1, IgG2, IgG3 or IgG4, or a mutated IgG constant region.

8. The antibody of claim 7, wherein the constant region is human.

9. The antibody according to claim 1, wherein the antibody is a Fab, a Fab', a F(ab')2, or an scFv.

10. An antibody drug conjugate comprising the antibody according to claim 1 conjugated to a drug moiety.

11. The antibody drug conjugate of claim 10, wherein the drug moiety comprises a pyrrolobenzodiazepine dimer.

12. A pharmaceutical composition comprising the antibody of claim 1 and a pharmaceutically acceptable diluent, carrier, or excipient.

13. A pharmaceutical composition comprising the antibody drug conjugate of claim 10 and a pharmaceutically acceptable diluent, carrier, or excipient.

* * * * *

SEQUENCE LISTING

<160> NUMBER OF SEQ ID NOS: 18

<210> SEQ ID NO 1

```
<211> LENGTH: 119
<212> TYPE: PRT
<213> ORGANISM: Artificial Sequence
<220> FEATURE:
<223> OTHER INFORMATION: synthetic construct

<400> SEQUENCE: 1

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Ser Asn Tyr
            20                  25                  30

Leu Met Asn Trp Val Lys Gln Arg Pro Glu Gln Asp Leu Asp Trp Ile
        35                  40                  45

Gly Arg Ile Asp Pro Tyr Asp Gly Asp Ile Asp Tyr Asn Gln Asn Phe
    50                  55                  60

Lys Asp Lys Ala Ile Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Tyr Gly Thr Ala Tyr Gly Val Asp Tyr Trp Gly Gln Gly
            100                 105                 110

Thr Ser Val Thr Val Ser Ser
        115

<210> SEQ ID NO 2
<211> LENGTH: 111
<212> TYPE: PRT
<213> ORGANISM: Artificial Sequence
<220> FEATURE:
<223> OTHER INFORMATION: synthetic construct

<400> SEQUENCE: 2

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Arg Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 3
<211> LENGTH: 119
<212> TYPE: PRT
<213> ORGANISM: Artificial Sequence
<220> FEATURE:
<223> OTHER INFORMATION: synthetic construct

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30
```

```
Leu Met Asn Trp Val Arg Gln Ala Pro Gly Gln Gly Leu Glu Trp Met
        35                  40                  45

Gly Arg Ile Asp Pro Tyr Asp Gly Asp Ile Tyr Asn Gln Asn Phe
 50                  55                  60

Lys Asp Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Tyr Gly Thr Ala Tyr Gly Val Asp Tyr Trp Gly Gln Gly
                100                 105                 110

Thr Ser Val Thr Val Ser Ser
            115

<210> SEQ ID NO 4
<211> LENGTH: 111
<212> TYPE: PRT
<213> ORGANISM: Artificial Sequence
<220> FEATURE:
<223> OTHER INFORMATION: synthetic construct

<400> SEQUENCE: 4

Glu Ile Val Leu Thr Gln Ser Pro Ala Thr Leu Ser Leu Ser Pro Gly
 1                5                  10                  15

Glu Arg Ala Thr Leu Ser Cys Arg Ala Ser Glu Ser Val Asp Asn Tyr
                 20                  25                  30

Gly Ile Ser Phe Met Asn Trp Tyr Gln Gln Lys Pro Gly Gln Ala Pro
             35                  40                  45

Arg Leu Leu Ile Tyr Ala Ala Ser Arg Gln Gly Ser Gly Ile Pro Asp
 50                  55                  60

Arg Phe Ser Gly Ser Gly Ser Gly Thr Asp Phe Thr Leu Thr Ile Ser
 65                  70                  75                  80

Arg Leu Glu Pro Glu Asp Phe Ala Val Tyr Tyr Cys Gln Gln Ser Lys
                 85                  90                  95

Glu Val Pro Trp Thr Phe Gly Gly Gly Thr Lys Leu Glu Ile Lys
                100                 105                 110

<210> SEQ ID NO 5
<211> LENGTH: 119
<212> TYPE: PRT
<213> ORGANISM: Artificial Sequence
<220> FEATURE:
<223> OTHER INFORMATION: synthetic construct

<400> SEQUENCE: 5

Gln Val Gln Leu Val Gln Ser Gly Ala Glu Val Lys Lys Pro Gly Ala
 1                5                  10                  15

Ser Val Lys Val Ser Cys Lys Ala Ser Gly Tyr Thr Phe Ser Asn Tyr
                 20                  25                  30

Leu Met Asn Trp Val Arg Gln Ala Pro Gly Gln Gly Leu Glu Trp Ile
             35                  40                  45

Gly Arg Ile Asp Pro Tyr Asp Gly Asp Ile Tyr Asn Gln Asn Phe
 50                  55                  60

Lys Asp Arg Ala Thr Leu Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Tyr Gly Thr Ala Tyr Gly Val Asp Tyr Trp Gly Gln Gly
                100                 105                 110
```

Thr Ser Val Thr Val Ser Ser
        115

<210> SEQ ID NO 6
<211> LENGTH: 119
<212> TYPE: PRT
<213> ORGANISM: Artificial Sequence
<220> FEATURE:
<223> OTHER INFORMATION: synthetic construct

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Leu Met Asn Trp Val Arg Gln Ala Pro Gly Gln Gly Leu Glu Trp Ile
        35                  40                  45

Gly Arg Ile Asp Pro Tyr Asp Gly Asp Ile Asp Tyr Asn Gln Asn Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Thr Ala Tyr Gly Val Asp Tyr Trp Gly Gln Gly
            100                 105                 110

Thr Ser Val Thr Val Ser Ser
        115

<210> SEQ ID NO 7
<211> LENGTH: 119
<212> TYPE: PRT
<213> ORGANISM: Artificial Sequence
<220> FEATURE:
<223> OTHER INFORMATION: synthetic construct

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Leu Met Asn Trp Val Arg Gln Ala Pro Gly Gln Gly Leu Glu Trp Met
        35                  40                  45

Gly Arg Ile Asp Pro Tyr Asp Gly Asp Ile Asp Tyr Asn Gln Asn Phe
    50                  55                  60

Lys Asp Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Thr Ala Tyr Gly Val Asp Tyr Trp Gly Gln Gly
            100                 105                 110

Thr Ser Val Thr Val Ser Ser
        115

<210> SEQ ID NO 8
<211> LENGTH: 119
<212> TYPE: PRT
<213> ORGANISM: Artificial Sequence
<220> FEATURE:
<223> OTHER INFORMATION: synthetic construct

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Leu Met Asn Trp Val Arg Gln Ala Pro Gly Gln Gly Leu Glu Trp Met
        35                  40                  45

Gly Arg Ile Asp Pro Tyr Asp Gly Asp Ile Asp Tyr Asn Gln Asn Phe
    50                  55                  60

Lys Asp Arg Val Thr Ile Thr Arg Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Thr Ala Tyr Gly Val Asp Tyr Trp Gly Gln Gly
            100                 105                 110

Thr Ser Val Thr Val Ser Ser
        115

<210> SEQ ID NO 9
<211> LENGTH: 111
<212> TYPE: PRT
<213> ORGANISM: Artificial Sequence
<220> FEATURE:
<223> OTHER INFORMATION: synthetic construct

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Ile Ser Phe Met Asn Trp Phe Gln Gln Lys Pro Gly Gln Ala Pro
        35                  40                  45

Arg Leu Leu Ile Tyr Ala Ala Ser Arg Gln Gly Ser Gly Ile Pro Asp
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 10
<211> LENGTH: 111
<212> TYPE: PRT
<213> ORGANISM: Artificial Sequence
<220> FEATURE:
<223> OTHER INFORMATION: synthetic construct

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Ile Ser Phe Met Asn Trp Phe Gln Gln Lys Pro Gly Gln Ala Pro
        35                  40                  45

Arg Leu Leu Ile Tyr Ala Ala Ser Arg Gln Gly Ser Gly Ile Pro Asp
    50                  55                  60

```
Arg Phe Ser Gly Ser Gly Ser Gly Thr Asp Phe Thr Leu Thr Ile Ser
 65                  70                  75                  80

Arg Leu Glu Pro Glu Asp Phe Ala Val Tyr Tyr Cys Gln Gln Ser Lys
                 85                  90                  95

Glu Val Pro Trp Thr Phe Gly Gly Gly Thr Lys Leu Glu Ile Lys
            100                 105                 110
```

<210> SEQ ID NO 11
<211> LENGTH: 111
<212> TYPE: PRT
<213> ORGANISM: Artificial Sequence
<220> FEATURE:
<223> OTHER INFORMATION: synthetic construct

<400> SEQUENCE: 11

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Glu Ser Val Asp Asn Tyr
                 20                  25                  30

Gly Ile Ser Phe Met Asn Trp Tyr Gln Gln Lys Pro Gly Gln Ala Pro
             35                  40                  45

Arg Leu Leu Ile Tyr Ala Ala Ser Arg Gln Gly Ser Gly Ile Pro Asp
 50                  55                  60

Arg Phe Ser Gly Ser Gly Ser Gly Thr Asp Phe Thr Leu Thr Ile Ser
 65                  70                  75                  80

Arg Leu Glu Pro Glu Asp Phe Ala Val Tyr Phe Cys Gln Gln Ser Lys
                 85                  90                  95

Glu Val Pro Trp Thr Phe Gly Gly Gly Thr Lys Leu Glu Ile Lys
            100                 105                 110
```

<210> SEQ ID NO 12
<211> LENGTH: 323
<212> TYPE: PRT
<213> ORGANISM: Homo sapiens

<400> SEQUENCE: 12

```
Asp Thr Glu Ile Lys Val Asn Pro Pro Gln Asp Phe Glu Ile Val Asp
  1               5                  10                  15

Pro Gly Tyr Leu Gly Tyr Leu Tyr Leu Gln Trp Gln Pro Pro Leu Ser
                 20                  25                  30

Leu Asp His Phe Lys Glu Cys Thr Val Glu Tyr Glu Leu Lys Tyr Arg
             35                  40                  45

Asn Ile Gly Ser Glu Thr Trp Lys Thr Ile Ile Thr Lys Asn Leu His
 50                  55                  60

Tyr Lys Asp Gly Phe Asp Leu Asn Lys Gly Ile Glu Ala Lys Ile His
 65                  70                  75                  80

Thr Leu Leu Pro Trp Gln Cys Thr Asn Gly Ser Glu Val Gln Ser Ser
                 85                  90                  95

Trp Ala Glu Thr Thr Tyr Trp Ile Ser Pro Gln Gly Ile Pro Glu Thr
            100                 105                 110

Lys Val Gln Asp Met Asp Cys Val Tyr Tyr Asn Trp Gln Tyr Leu Leu
            115                 120                 125

Cys Ser Trp Lys Pro Gly Ile Gly Val Leu Leu Asp Thr Asn Tyr Asn
        130                 135                 140

Leu Phe Tyr Trp Tyr Glu Gly Leu Asp His Ala Leu Gln Cys Val Asp
145                 150                 155                 160
```

```
Tyr Ile Lys Ala Asp Gly Gln Asn Ile Gly Cys Arg Phe Pro Tyr Leu
            165                 170                 175
Glu Ala Ser Asp Tyr Lys Asp Phe Tyr Ile Cys Val Asn Gly Ser Ser
        180                 185                 190
Glu Asn Lys Pro Ile Arg Ser Ser Tyr Phe Thr Phe Gln Leu Gln Asn
    195                 200                 205
Ile Val Lys Pro Leu Pro Pro Val Tyr Leu Thr Phe Thr Arg Glu Ser
210                 215                 220
Ser Cys Glu Ile Lys Leu Lys Trp Ser Ile Pro Leu Gly Pro Ile Pro
225                 230                 235                 240
Ala Arg Cys Phe Asp Tyr Glu Ile Glu Ile Arg Glu Asp Asp Thr Thr
                245                 250                 255
Leu Val Thr Ala Thr Val Glu Asn Glu Thr Tyr Thr Leu Lys Thr Thr
            260                 265                 270
Asn Glu Thr Arg Gln Leu Cys Phe Val Val Arg Ser Lys Val Asn Ile
        275                 280                 285
Tyr Cys Ser Asp Asp Gly Ile Trp Ser Glu Trp Ser Asp Lys Gln Cys
    290                 295                 300
Trp Glu Gly Glu Asp Leu Ser Lys Lys Thr Leu Leu Arg His His His
305                 310                 315                 320
His His His

<210> SEQ ID NO 13
<211> LENGTH: 5
<212> TYPE: PRT
<213> ORGANISM: Artificial Sequence
<220> FEATURE:
<223> OTHER INFORMATION: synthetic construct

<400> SEQUENCE: 13

Asn Tyr Leu Met Asn
1               5

<210> SEQ ID NO 14
<211> LENGTH: 17
<212> TYPE: PRT
<213> ORGANISM: Artificial Sequence
<220> FEATURE:
<223> OTHER INFORMATION: synthetic construct

<400> SEQUENCE: 14

Arg Ile Asp Pro Tyr Asp Gly Asp Ile Asp Tyr Asn Gln Asn Phe Lys
1               5                   10                  15
Asp

<210> SEQ ID NO 15
<211> LENGTH: 10
<212> TYPE: PRT
<213> ORGANISM: Artificial Sequence
<220> FEATURE:
<223> OTHER INFORMATION: synthetic construct

<400> SEQUENCE: 15

Gly Tyr Gly Thr Ala Tyr Gly Val Asp Tyr
1               5                   10

<210> SEQ ID NO 16
<211> LENGTH: 15
<212> TYPE: PRT
<213> ORGANISM: Artificial Sequence
<220> FEATURE:
```

```
<223> OTHER INFORMATION: synthetic construct

<400> SEQUENCE: 16

Arg Ala Ser Glu Ser Val Asp Asn Tyr Gly Ile Ser Phe Met Asn
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: synthetic construct

<400> SEQUENCE: 17

Ala Ala Ser Arg Gln Gly Ser
1               5

<210> SEQ ID NO 18
<211> LENGTH: 9
<212> TYPE: PRT
<213> ORGANISM: Artificial Sequence
<220> FEATURE:
<223> OTHER INFORMATION: synthetic construct

<400> SEQUENCE: 18

Gln Gln Ser Lys Glu Val Pro Trp Thr
1               5
```